(12) United States Patent
Jayaram et al.

(10) Patent No.: US 9,133,230 B2
(45) Date of Patent: Sep. 15, 2015

(54) HYDRAZONE DERIVATIVES HAVING POTENT ANTITUMOR ACTIVITY TOWARD MULTI-DRUG RESISTANT TUMOR CELLS

(75) Inventors: Hiremagular N. Jayaram, Indianapolis, IN (US); Praveen Kusumanchi, Indianapolis, IN (US); Mario Grifantini, Camerino (IT); Palmarisa Franchetti, Camerino (IT); Loredana Cappellacci, Camerino (IT); Riccardo Petrelli, Camerino (IT)

(73) Assignee: THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 224 days.

(21) Appl. No.: 13/530,086

(22) Filed: Jun. 21, 2012

(65) Prior Publication Data
US 2012/0329747 A1   Dec. 27, 2012

Related U.S. Application Data

(60) Provisional application No. 61/499,519, filed on Jun. 21, 2011.

(51) Int. Cl.
| | |
|---|---|
| A61K 31/7076 | (2006.01) |
| A61K 31/52 | (2006.01) |
| A61P 35/00 | (2006.01) |
| C07H 19/167 | (2006.01) |
| C07D 473/34 | (2006.01) |
| A61K 31/122 | (2006.01) |
| A61K 31/337 | (2006.01) |
| A61K 31/44 | (2006.01) |

(52) U.S. Cl.
CPC ............ *C07H 19/167* (2013.01); *A61K 31/122* (2013.01); *A61K 31/337* (2013.01); *A61K 31/44* (2013.01); *A61K 31/52* (2013.01); *A61K 31/7076* (2013.01); *C07D 473/34* (2013.01)

(58) Field of Classification Search
None
See application file for complete search history.

(56) References Cited

U.S. PATENT DOCUMENTS 4,938,949 A     7/1990   Borch et al.

FOREIGN PATENT DOCUMENTS

WO   WO 2010074746   * 7/2010   ............. A01N 57/00

OTHER PUBLICATIONS

Ettmayer, P. et al., Journal of Medicinal Chemistry, "Lessons Learned from Marketed and Investigational Prodrugs", 2004, vol. 47, No. 10, pp. 2393-2404.*
Fleysher, H. M. et al., Nucleic Acid Chemistry: The Synthesis of an Adenosine Derivative Containing a "Nitrogen Mustard" Moiety at N-6, 1979, vol. 2, pp. 667-671.*
Stella, Valentino, Expert Opinion on Therapeutic Patents, "Prodrugs as Therapeutics", 2004, vol. 14, No. 3, pp. 277-280.*
Testa, Bernard, Biochemical Pharmacology, "Prodrug research: futile or fertile?", 2004, vol. 68, pp. 2097-2106.*
Wolff, Manfred E., Burger's Medicinal Chemistry and Drug Discovery, Fifth Edition, vol. 1: Principles and Practice, 1994, pp. 975-977.*
Zips, Daniel et al., In Vivo, "New Anticancer Agents: In Vitro and In Vivo Evaluation", 2005, vol. 19, pp. 1-8.*
Agrawal et al., Prog. Med. Chem., 1978, 321-356, 15.
Antonini et al., J. Med. Chem., 1981, 1181-1184, 24(10).
Berge et al., J. Pharm. Sci., 1977, 1-19, 66(1).
Cappellacci et al., J. Med. Chem., 2002, 1196-1202, 45(6).
Cappellacci et al., J. Med. Chem., 2005, 1550-1562, 48(5).
Cappellacci et al., Coll. Czech. Chem. Comm., 2006, 1088-1098, 71(7).
Cappellacci et al., Bioorg. Med. Chem., 2008, 336-353, 16(1).
Cappellacci et al., J. Med. Chem., 2008, 4260-4269, 51(15).
Cappellacci et al., Eur. J. Med. Chem., 2011, 1499-1504, 46(5).
Cerqueira et al., Recent Pat. Anticancer Drug Discov., 2007, 11-29, 2(1).
Cory et al., Anticancer Res., 1994, 875-879, 14(3).
Easmon et al., Heterocycles, 1989, 1399-1408, 29(7).
Easmon et al., J. Med. Chem., 1997, 4420-4425, 40(26).
Easmon et al., J. Med. Chem., 2006, 6343-6350, 49(21).
Eliel, Stereochemistry of Carbon Compounds,1962, McGraw Hill (Table of Contents).
Finch et al., Biochem. Pharmacol., 2000, 983-991, 59(8).
Finch et al., Adv.Enzyme Regul., 1999, 3-12, 39(1).
Fox, Pharmac. Ther., 1985, 31-42, 30(1).
Franchetti et al., J. Med. Chem., 1998, 1708-1715, 41(10).
Franchetti et al., J. Med. Chem., 2005, 4983-4989, 48(15).
Gennaro (Ed.), Remington's Pharmaceutical Sciences 18th ed., 1990, 1138-1162.
Gennaro (Ed.), Remington: The Science and Practice of Pharmacy 20th ED., 2000, vol. II, Mack Publishing Company, Easton, PA (Table of Contents).
Graci et al., Antimicrob. Agents Chemother., 2008, 971-979, 52(3).
Horiuchi et al., Bioorg. Med. Chem. Lett., 2009, 305-308, 19(2).
Jacques et al., Enantiomers, Racemates and Resolutions, 1981, Wiley-Interscience, NY (Table of Contents).
Kowol et al., J. Biol., Inorg. Chem., 2011, 409-423, 17(3).
Lochmuller et al., J. Chromatogr. A, 1975, 283-302, 113(3).
Matsuo et al., Tetrahedron, 2003, 6739-6750, 59(35).
Meli et al., Int. J. Oncol., 2011, 1427-1436, 38(5).
Nocentini et al., Cancer Res., 1993, 19-26, 53(1).
Ogretman et al., Biochemistry, 2000, 194-204, 39(1).
Paull et al., J. Natl. Cancer Inst., 1989, 1088-1092,81(14).
Richardson et al., J. Med. Chem., 2006, 6510-6521, 49(22).

(Continued)

*Primary Examiner* — Shaojia Anna Jiang
*Assistant Examiner* — Bahar Craigo
(74) *Attorney, Agent, or Firm* — Acuity Law Group, P.C.; Daniel M. Chambers

(57) ABSTRACT

A patentable new class of hydrazone derivative compounds is described, as are methods for synthesizing such compounds. The hydrazones of the invention can be used, for example, as potent anti-cancer agents, including to inhibit the growth of cancer cells that exhibit multidrug resistance.

3 Claims, 2 Drawing Sheets

(56) References Cited

OTHER PUBLICATIONS

Shao et al., Curr. Cancer Drug Targets, 2006, 409-431, 6(5).
Shen et al., Mol. Cell. Biol., 1986, 4039-4044, 6(11).
Weinstein et al., Science, 1997, 343-349, 275(5298).
Whitnall et al., Proc. Natl. Acad. Sci., 2006, 14901-14906, 103(40).
Wilen et al., Tetrahedron, 1977, 2725-2736, 33(21).
Yu et al., J. Med. Chem., 2009, 5271-5294, 52(17).
Kowol et al., J. Biol., Inorg. Chem., 2012, 409-423, 17(3).

* cited by examiner

HYDRAZONE DERIVATIVES HAVING POTENT ANTITUMOR ACTIVITY TOWARD MULTI-DRUG RESISTANT TUMOR CELLS

RELATED APPLICATION

This patent application claims the benefit of and priority to U.S. provisional patent application Ser. No. 61/499,519, filed on 21 Jan. 2011, which is incorporated herein in its entirety for any all purposes.

GOVERNMENT SPONSORSHIP

This invention was made with U.S. government support under a VA Merit Review grant entitled, "Targeted chemogene therapy for colorectal cancer", naming Hiremagular N. Jayaram as principal investigator. Accordingly, the U.S. government may have certain rights in the invention(s) claimed herein.

FIELD OF THE INVENTION

The present invention relates to the preparation of a novel class of hydrazone derivatives prepared from 6-hydrazinopurine and $N^6$-amino-adenosine, as well as their utilization as useful therapeutic anti-cancer agents, including inhibiting the growth of cancer cells exhibiting multidrug resistance.

BACKGROUND OF THE INVENTION

1. Introduction

The following description includes information that may be useful in understanding the present invention. It is not an admission that any of the information provided herein, or any publication specifically or implicitly referenced herein, is prior art, or even particularly relevant, to the presently claimed invention.

2. Background

Conventional cancer treatments include radiotherapy, chemotherapy, and surgery. Recently, the clinical outcome of cancer patients has improved dramatically with combination chemotherapy, and today anticancer research is centering on developing targeted and individualized therapies. Even so, current treatments often do not completely rid patients of their cancers and thus significant challenges remain.

Some chemical antitumor agents that are undergoing clinical evaluation produce low response rates in solid tumors. High cytotoxicity also often occurs as a serious side effect of chemotherapy. Additionally, cancer cells can become resistant to various chemotherapeutic agents directed at them, so overcoming this drug-resistance through the provision of new anticancer agents is an important research focus. For this reason development of novel chemotherapeutic agents for treatment of some cancer types that can become refractory and/or show little responsiveness to current chemotherapy (e.g., colon, prostate, ovarian, and renal cancer, non-small cell lung carcinoma, CNS cancers, and melanoma) is urgently needed.

Ribonucleotide reductase (RR), a critical enzyme for the synthesis of deoxyribonucleotides and cell division, is overexpressed in rapidly dividing cancer cells, making it an important target for cancer therapy (Cerqueira, et al., *Recent Pat. Anticancer Drug Discov.*, vol. 2, 11-29 (2007)). The enzyme is composed of a complex of two subunits, named R1 and R2. The R1 subunit contains the active site, including an essential cysteine designed to become a thiyl radical, and allosteric sites, while the R2 subunit contains a diferric-tyrosyl radical cofactor (Shao, et al., *Curr. Cancer Drug Targ.*, vol. 6, 409-431 (2006)).

There are three broad classes of RR inhibitors. The first class includes nucleoside analogues, which bind to the R1 subunit of the enzyme (Cerqueira, et al., above). Many nucleoside analogues that inhibit R1 subunit activity have been approved for human clinical treatment of cancer, and others are being evaluated in clinical trials (Shao, et al., above).

The second RR inhibitor class is mainly made up of short chain peptides that bind at the interface of the R1 and R2 subunits, thereby interfering with the enzyme activity (Yvan, et al., EP 0383190 (Bio-mega, Inc.), 1990). The third class of RR inhibitors binds with high affinity to the nonheme iron in the R2 subunit (Fox, R. M., in *Inhibitors of Ribonucleotide Reductase Activity*; Cory, J. G., Cory, A. H., Eds.; Pergamon Press: Oxford, 1989; pp 113-125).

RR inhibitors such as hydroxyurea, didox (3,4-dihydroxybenzohydroxamic acid), trimidox (3,4,5-trihydroxybenzamidoxime), and nitric oxide target the small R2 subunit by directly quenching the tyrosyl radical and/or affecting the iron center (Shao, et al., above). Other R2 inhibitors belong to the class of powerful iron chelators that coordinate with iron through an N*—N*—S* [heterocyclic carboxaldehyde thiosemicarbazones (Agrawal, et al., *Prog. Med. Chem.*, vol. 15, 321-356 (1978)), such as Triapine (3-aminopyridine-2-carboxaldehyde thiosemicarbazone) (Finch, et al., *Adv. Enzyme Regul.*, vol. 39, 3-12 (1999); Finch, et al., *Biochem. Pharmacol.* 59, 983-991 (2000)), and 2,2'-Bipyridyl-6-carbothioamide (BPYTA) (Antonini, et al., *J. Med. Chem.*, vol. 24, 1181-1184 (1981); Nocentini, et al., *Cancer Res.*, vol. 53, 19-26 (1993)). Also, iron chelators that coordinate with iron through an N*—N*—N* tridentate ligand system, such as N-heteroarylhydrazones, are potent R2 inhibitors (Cory, et al., *Anticancer Res.*, vol. 14, 875-880 (1994); Easmon, et al., *J. Med. Chem.*, vol. 40, 4420-4425 (1997); Easmon, et al., *J. Med. Chem.*, vol. 49, 6343-6350 (2006)). Several azinyl hydrazones containing a N*—N*—N* structural motif have also be reported to inhibit tumor cell growth by cytotoxic mechanisms other than RR inhibition (Whitnall, et al., *PNAS*, vol. 103, 14901-14906 (2006); Richardson, et al., *J. Med. Chem.* 49, 6510-6521 (2006); Yu, et al., *J. Med. Chem.* 52, 5271-5294 (2009); Horiuchi, et al., *Bioorg. Med. Chem. Lett.*, vol. 19, 305-308 (2009)).

It has also been reported that an $N^6$-substituted adenosine (6-hydrazinopurine-riboside, compound 1, below) and 3'-C-methyl-adenosine (3'-Me-Ado) derivatives are effective cytotoxic agents against various human tumor cell lines (HeLa, HT-29, K562, and MCF-7) (Cappellacci, et al., *Eur. J. Med. Chem.*, vol. 46, 1499-1504 (2011); Cappellacci, et al., *J. Med. Chem.*, vol. 51, 4260-4269 (2008)).

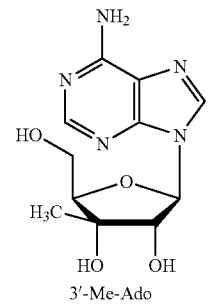

3'-Me-Ado

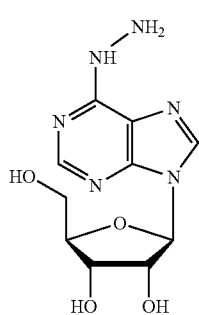

6-Hydrazinopurine-riboside has recently been reported to be a potent mutagenic agent (Graci, et al., *Antimicrob. Agents Chemother.*, vol. 52, 971-979 (2008)), and as inhibiting human RR, possibly by scavenging tyrosyl free radicals involved in the reduction of nucleoside diphosphates.

3'-C-Methyl-adenosine is a purine ribonucleoside that acts as a mechanism-based inhibitor of R1 subunit of mammalian RR, and reportedly has significant antitumor activity against a panel of human leukemia and carcinoma cell lines (Franchetti, et al., *J. Med. Chem.*, vol. 48, 4983-4989 (2005); Cappellacci, et al., *J. Med. Chem.*, vol. 51, 4260-4269 (2008)).

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

An "agent" refers to an active ingredient delivered to achieve an intended therapeutic benefit.

The term "combination therapy" refers to a therapeutic regimen that involves the provision of at least two distinct therapies to achieve an indicated therapeutic effect. For example, a combination therapy may involve the administration of two or more chemically distinct active ingredients, or agents, for example, a hydrazone derivative according to the invention and another chemotherapeutic agent. Alternatively, a combination therapy may involve the administration of one or more hydrazone derivatives, alone or in conjunction with another agent as well as the delivery of another therapy. In the context of the administration of two or more chemically distinct agents, it is understood that the active ingredients may be administered as part of the same composition or as different compositions. When administered as separate compositions, the compositions comprising the different active ingredients may be administered at the same or different times, by the same or different routes, using the same or different dosing regimens, all as the particular context requires and as determined by the attending physician. Similarly, when one or more agents are combined with other drugs, the drug(s) may be delivered before, during, and/or after the period the subject is in therapy.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, such solids include dried compositions prepared by lyophilization, freeze-drying, precipitation, and similar procedures.

"Monotherapy" refers to a treatment regimen based on the delivery of one therapeutically effective compound, whether administered as a single dose or several doses over time.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

The term "species" when used in the context of describing a particular drug species, refers to a population of chemically indistinct molecules.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

SUMMARY OF THE INVENTION

This invention concerns a patentable new class of hydrazone derivatives of purines and 9-β-ribofuranosyl-purines and analogues modified at the 3'-position of the sugar moiety that combine 3'-C-methyl-ribose and N*—N*—N* tridentate ligand system structural features to inhibit mammalian, particular human, ribonucleotide reductase activity. Such compounds can be used as potent anticancer chemotherapeutic agents, particularly to treat multidrug-resistant tumors, as well as to treat bacterial infections (e.g., tuberculosis and malaria), including infections by multidrug resistant bacteria.

Thus, in one aspect, the invention concerns patentable hydrazone compounds of the general formula (I):

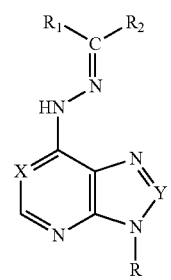

wherein X=N or CH; Y=N or C=$R_3$ where $R_3$=H, alkyl, cycloalkyl, phenyl, or substituted phenyl, benzyl or substituted benzyl, F, Cl, Br, I; R=H, alkyl, cycloalkyl, phenyl, or substituted phenyl, benzyl, 2-hydroxyethyl, 3-hydroxypropyl, 2,3-dihydroxypropyl, alkoxyalkyl, carboxyalkyl and related esters.

R may be also:

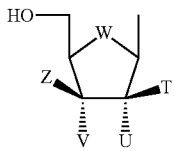

wherein W=O, S or $CH_2$; U=H, OH, F, Cl; V=H, OH, F, Cl; T=H, $CH_3$, F, Cl or OH; Z=H, $CH_3$, OH, F, Cl.

$R_1$ in compound of general formula I may be:

H, alkyl, cycloalkyl, phenyl, benzyl, dihydroxyethyl, dihydroxypropyl, carboxy, carboxyalkyl, $COOR_3$, $(CH_2)_n COOR_3$ where $R_3$ is an aliphatic residue or a phenyl group;

$R_1$ may be also one of the following heterocycles:

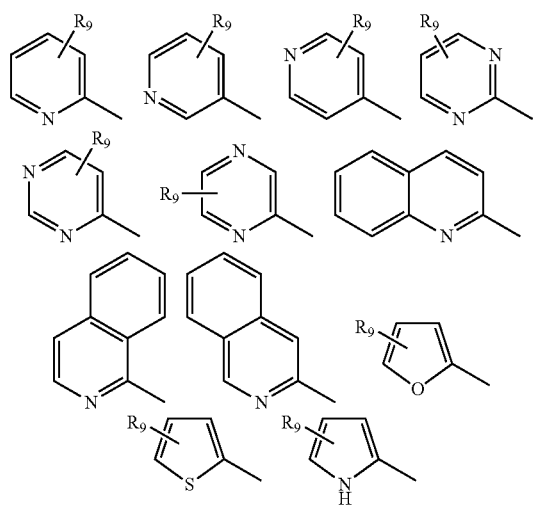

wherein $R_9$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=$NH(NHOH)$, COOH or $COOR_6$, wherein $R_6$=an aliphatic residue or a phenyl group, or $CONR_7R_8$, wherein $R_7$, $R_8$ represent H, an aliphatic substituent or a phenyl group.

$R_2$ in compound of general formula I may be:

H, alkyl, cycloalkyl, phenyl, benzyl, dihydroxyethyl, dihydroxypropyl, carboxy, carboxyalkyl, $COOR_3$, $(CH_2)_n COOR_3$ where $R_3$ an aliphatic residue or a phenyl group.

$R_2$ may be also one of the following heterocycles:

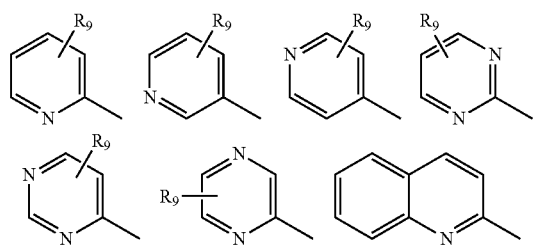

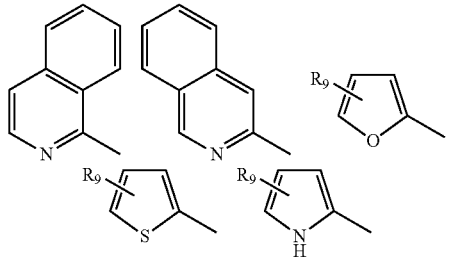

wherein $R_9$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=$NH(NHOH)$, COOH or $COOR_6$, wherein $R_6$=an aliphatic residue or a phenyl group, or $CONR_7R_8$, wherein $R_7$, $R_8$ represent H, an aliphatic substituent or a phenyl group.

In the context of the invention, the term "alkyl" means a branched or unbranched, saturated or unsaturated, monovalent or multivalent hydrocarbon group. Examples of alkyl include, but are not limited to, methyl, ethyl, propyl, isopropyl, butyl, isobutyl, t-butyl, pentyl, hexyl, heptyl, decyl, ethenyl, propenyl, butenyl, isobutenyl, pentenyl, hexenyl, heptenyl, octenyl, nonenyl, decenyl, ethynyl, propynyl, butynyl, isobutynyl, pentynyl, hexynyl, heptynyl, octynyl, nonynyl, and decynyl.

In the context of the invention, the term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, cycloalkyl groups such as cyclopropyl, cyclobutyl, cyclopentyl, cyclohexyl, and cycloheptyl, and saturated cyclic and bicyclic terpenes and cycloalkenyl groups such as cyclopropenyl, cyclobutenyl, cyclopentenyl, cyclohexenyl, cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

In the context of the invention, the term "phenyl" means also substituted or disubstituted phenyl group:

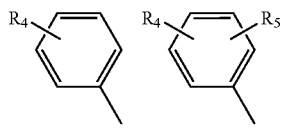

wherein $R_4$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=$NH(NHOH)$, COOH or $COOR_6$, wherein $R_6$=an aliphatic residue or a phenyl group, or $CONR_7R_8$, wherein $R_7$, $R_8$ represent H, an aliphatic substituent or a phenyl group. $R_5$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=$NH(NHOH)$, COOH or $COOR_6$, wherein $R_6$=an aliphatic residue or a phenyl group, or $CONR_7R_8$, wherein $R_7$, $R_8$ represent H, an aliphatic substituent or a phenyl group.

A related aspect of the invention concerns compositions, which comprise a compound of the invention in combination with a carrier. Such compositions can be in liquid or dry form. In the context of therapy, such compositions preferably are pharmaceutically acceptable formulations.

Another aspect of the invention relates to the preparation of the compounds of the invention, including syntheses from 6-hydrazino-purine, 6-hydrazino-1-deazapurine, or 6-hydrazino-8-azapurine.

Yet another aspect of the invention relates to methods of administering the compositions of the invention. A related aspect concerns the use of the hydrazone derivatives of the invention as therapeutic agents, in particular as anti-cancer therapeutic agents. The novel hydrazone derivatives of purine and purine-nucleosides are also active against multidrug-resistant cancer cells. Cancers that may be treated with compounds of the invention, alone or in combination with other drugs or therapies (e.g., surgery, radiation, etc.) include breast, cervical, colorectal, and liver cancers, including breast adenocarcinomas, cervical adenocarcinomas, and hepatocellular carcinomas. Combination therapies include administration of therapeutically effective amounts of a compound according to the invention as well as another drug, for example, another chemotherapeutic agent, for example, Shikonin, Taxol, or Sorafenib.

These and other aspects of the invention are described below.

DETAILED DESCRIPTION OF THE INVENTION

Compounds

Figure 1:
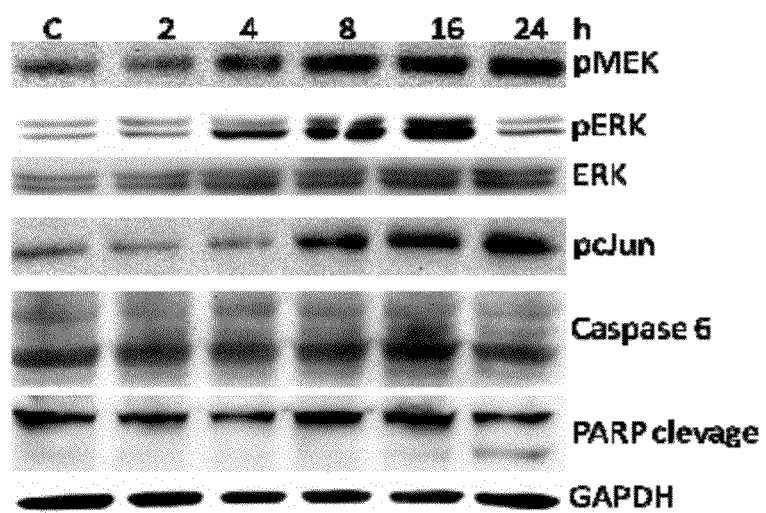
FIG. 1 is a gel showing the effects of compound RPC042 on HT29 cells.

The present invention is based on the invention of a patentable new class of purine analog compounds, namely those represented by general formula (I):

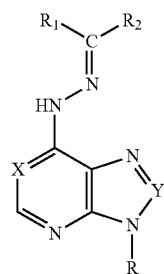

I wherein X=N or CH; Y=N or C—$R_3$ where $R_3$=H, alkyl, cycloalkyl, phenyl, or substituted phenyl, benzyl or substituted benzyl, F, Cl, Br, I; R=H, alkyl, cycloalkyl, phenyl, or substituted phenyl, benzyl, 2-hydroxyethyl, 3-hydroxypropyl, 2,3-dihydroxypropyl, alkoxyalkyl, carboxyalkyl and related esters.

R may be also:

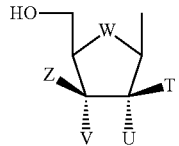

wherein W=O, S or $CH_2$; U=H, OH, F, Cl; V=H, OH, F, Cl; T=H, $CH_3$, F, Cl or OH; Z=H, $CH_3$, OH, F, Cl.

$R_1$ in compound of general formula I may be:
H, alkyl, cycloalkyl, phenyl, benzyl, dihydroxyethyl, dihydroxypropyl, carboxy, carboxyalkyl, $COOR_3$, $(CH_2)_n COOR_3$ where $R_3$ is an aliphatic residue or a phenyl group;

$R_1$ may be also one of the following heterocycles:

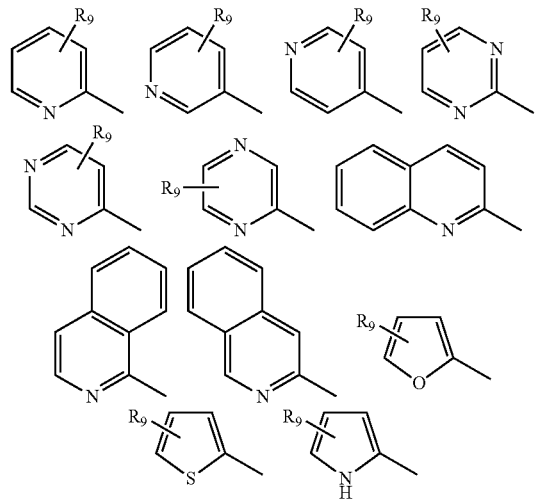

wherein $R_9$=H, $CH_3$, $OCH_3$, OH, Cl, Br, F, $CF_3$, $NO_2$, $NH_2$, $NHCOCH_3$, $N(CH_3)_2$, CN, C=NH($NH_2$), C=S($NH_2$), C=NH(NHOH), COOH or $COOR_6$, wherein $R_6$=an aliphatic residue or a phenyl group, or $CONR_7R_8$, wherein $R_7$, $R_8$ represent H, an aliphatic substituent or a phenyl group.

$R_2$ in compound of general formula I may be:
H, alkyl, cycloalkyl, phenyl, benzyl, dihydroxyethyl, dihydroxypropyl, carboxy, carboxyalkyl, $COOR_3$, $(CH_2)_n COOR_3$ where $R_3$ an aliphatic residue or a phenyl group.

$R_2$ may be also one of the following heterocycles:

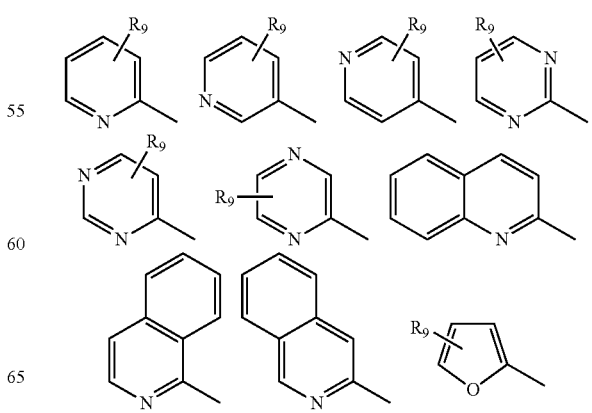

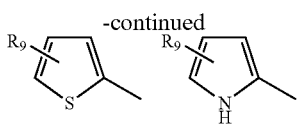

wherein $R_9$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=NH(NHOH), COOH or $COOR_6$, wherein $R_6$=an aliphatic residue or a phenyl group, or $CONR_7R_8$, wherein $R_7$, $R_8$ represent H, an aliphatic substituent or a phenyl group.

In the context of the invention, the term "alkyl" means a branched or unbranched, saturated or unsaturated, monovalent or multivalent hydrocarbon group. Examples of alkyl include, but are not limited to, methyl, ethyl, propyl, isopropyl, butyl, isobutyl, t-butyl, pentyl, hexyl, heptyl, decyl, ethenyl, propenyl, butenyl, isobutenyl, pentenyl, hexenyl, heptenyl, octenyl, nonenyl, decenyl, ethynyl, propynyl, butynyl, isobutynyl, pentynyl, hexynyl, heptynyl, octynyl, nonynyl, and decynyl.

In the context of the invention, the term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, cycloalkyl groups such as cyclopropyl, cyclobutyl, cyclopentyl, cyclohexyl, and cycloheptyl, and saturated cyclic and bicyclic terpenes and cycloalkenyl groups such as cyclopropenyl, cyclobutenyl, cyclopentenyl, cyclohexenyl, cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

In the context of the invention, the term "phenyl" means also substituted or disubstituted phenyl group:

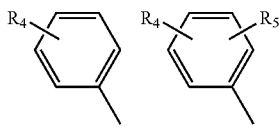

wherein $R_4$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=NH(NHOH), COOH or $COOR_6$, wherein $R_6$=an aliphatic residue or a phenyl group, or $CONR_7R_8$, wherein $R_7$, $R_8$ represent H, an aliphatic substituent or a phenyl group. $R_5$=H, $CH_3$, $OCH_3$, OH, Cl, Br, F, $CF_3$, $NO_2$, $NH_2$, $NHCOCH_3$, $N(CH_3)_2$, CN, C=$NH(NH_2)$, C=$S(NH_2)$, C=NH(NHOH), COOH or $COOR_6$, wherein $R_6$=an aliphatic residue or a phenyl group, or $CONR_7R_8$, wherein $R_7$, $R_8$ represent H, an aliphatic substituent or a phenyl group.

As used herein unless otherwise specified, the term "substituted" in reference to a group, moiety, and the like refers to one having one or more substituent groups each independently selected from hydrogen, alkyl, alkenyl, alkoxy, hydroxy, nitro, amino, alkylamino, cyano, halogen, thiol, aryl, cycloalkyl, heteroaryl, heterocycloalkyl (e.g., piperidinyl, morpholino, pyrrolidinyl), imino, hydroxyalkyl, aryloxy, and arylalkyl, preferably hydrogen, alkyl, alkenyl, alkoxy, hydroxy, nitro, amino, alkylamino, halo, thiol, and aryloxy, more preferably hydrogen, alkyl, alkenyl, alkoxy, hydroxy, nitro, amino, alkylamino, and halogen, even more preferably hydrogen, alkyl, and alkoxy, and most preferably alkoxy.

The compounds of the invention are preferably prepared as salts. The term "salt" refers to a cationic salt formed at any acidic (e.g., carboxyl) group, or an anionic salt formed at any basic (e.g., amino) group. Many salts are known in the art. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). When intended for administration to a subject, such salts should be appropriate for such use. Thus, the term "pharmaceutically acceptable" means suitable for use in humans, whereas "veterinarily acceptable" means suitable for use in non-human animals, particularly non-human mammals.

The term "pharmaceutically acceptable salt" refers to salts which retain the biological effectiveness and properties of the compounds of the invention and which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts, see, e.g., Berge, et al. (*J. Pharm. Sci.*, vol. 66, 1 (1977)).

The expression "non-toxic pharmaceutically acceptable salts" non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, fumaric, methanesulfonic, trifluoromethanesulfonic, and toluenesulfonic acid and the like. Salts also include those from inorganic bases, such as ammonia, sodium hydroxide, potassium hydroxide, and hydrazine. Suitable organic bases include methylamine, ethylamine, propylamine, dimethylamine, diethylamine, diethanolamine, trimethylamine, triethylamine, triethanolamine, ethylenediamine, hydroxyethylamine, morpholine, piperazine, and guanidine.

As those in the art will appreciate, where any variable, moiety, group, or the like occurs more than one time in any variable or structure, its definition at each occurrence is independent of its definition at every other occurrence. All percentages, ratios, and proportions used herein are by weight unless otherwise specified. Specific and preferred values listed below for radicals, substituents, and ranges, are for illustration only, and they do not exclude other defined values or other values within defined ranges for the radicals and substituents. The compounds of the invention are patentable compounds of general formula I having any combination of the values, specific values, more specific values, and preferred values described herein.

The present invention also includes other forms of the compounds of the invention, including prodrug and polymorph forms. Here, a "prodrug" is a compound that contains one or more functional groups that can be removed or modified in vivo to result in a molecule that can exhibit therapeutic utility in vivo. A "polymorph" refers to a compound that has an identical chemical composition (i.e., it is of the same compound species) as compared to another compound but that differs in crystal structure.

Synthesis

The compounds of the invention can be prepared by any suitable synthetic or semi-synthetic method. In the event a compound of the invention has an asymmetric carbon atom, optical isomers exist. As such, the invention encompasses mixtures of the optical isomers, as well as each of the two enantiomer species of such compound. If desired, the resolution of racemic compounds of can be accomplished using conventional means, such as the formation of a diastereomeric salt with an optically active resolving amine; see, for example, "Stereochemistry of Carbon Compounds," by E. L. Eliel (McGraw Hill, 1962); Lochmuller, et al., *J Chromatog.*, vol. 113, 283 (1975); "Enantiomers, Racemates and Resolutions," by J. Jacques, A. Collet, and S. H. Wilen, (Wiley-Interscience, New York, 1981); Wilen, et al., *Tetrahedron*, vol. 33, 2725-2736 (1977).

In preferred synthetic methods, hydrazone derivatives of the invention as represented by general formula (I) were synthesized by heating equimolecular amount of hydrazines (II) with an aldehyde (III) or a ketone (IV) in methanol or ethanol in the presence of a catalytic amount of glacial acetic acid. The reaction was monitored by TLC ($CHCl_3$/MeOH 9:1). The reaction mixture was cooled to 4° C. overnight. The formed precipitates were filtered and recrystallized. When there were no precipitates formed, the reaction mixtures were evaporated to dryness and the residues were recrystallized from the appropriate solvents or purified by chromatography to obtain the pure hydrazones.

The hydrazines of type II were prepared by reaction of the respective 6-chloro analogues (V) with 98% hydrazine hydrate at room temperature or by heating.

The aldehydes or ketones of type III and IV were synthesized utilizing known methods or patent literature (see Mukaiyama, et al., *Tetrahedron*, vol. 59, 6739-6750 (2003); Lutz, et al., DE 43 06 006-A).

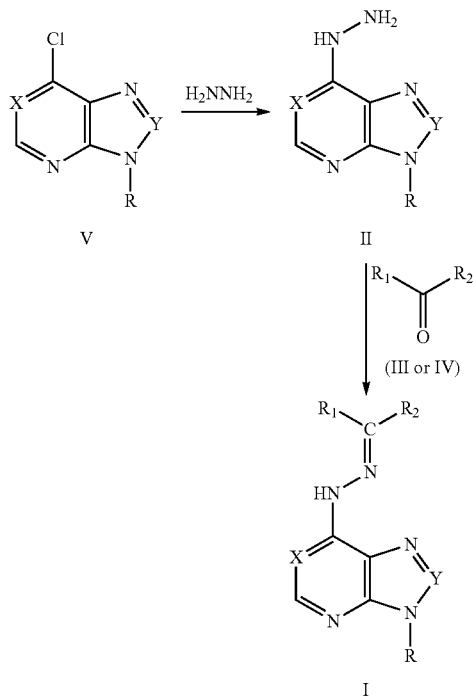

Considering the fact that when $R_1$ and $R_2$ in hydrazones of type I are different, the compounds can exist as the E- or Z-isomers, or as E/Z-mixtures, a detailed examination of the stereochemistry at the —C=N— bond was performed. The configuration of the isolated compounds was determined by $^1H$ NMR spectroscopy and NOE-difference experiments in analogy to the reported findings related to thiosemicarbazones (Easmon, et al., *Heterocycles*, vol. 29, 1399-1408 (1989)). Most of the synthesized hydrazones were found to be E isomers.

The compounds of the invention can also be prepared in the form of their pharmaceutically acceptable salts or their non-pharmaceutically acceptable salts. The non-pharmaceutically acceptable salts are useful as intermediates for the preparation of pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Compositions

As described throughout this specification, the compounds of the invention are useful as therapeutic agents. The compounds will generally be formulated so as to be amenable to administration to a subject by the chosen route. Thus, a further aspect of this invention concerns compositions, particularly pharmaceutical or veterinary compositions, comprising a hydrazone derivative, such as, for example, a compound represented by general formula I, or an acceptable salt, base, or prodrug form thereof, formulated together with one or more non-toxic acceptable carriers, preferably pharmaceutically acceptable carriers. The terms "pharmaceutically acceptable carrier" and "physiologically acceptable carrier" refer to molecular entities and compositions that are physiologically tolerable and do not typically produce an unintended allergic or similar untoward reaction, such as gastric upset, dizziness and the like, when administered to a subject. In the context of therapeutic compositions intended for human administration, pharmaceutically acceptable carriers are used. The compounds of the invention may be processed in accordance with conventional methods of pharmaceutical compounding techniques to produce medicinal agents (i.e., medicaments or therapeutic compositions) for administration to subjects, including humans and other mammals, i.e., "pharmaceutical" and "veterinary" administration, respectively. See, for example, the latest edition of Remington's Pharmaceutical Sciences (Mack Publishing Co., Easton, Pa.). Typically, a compound such as a hydrazone derivative is combined as a composition with a pharmaceutically acceptable carrier. The composition(s) may also include one or more of the following: excipients; preserving agents; solubilizing agents; stabilizing agents; wetting agents; emulsifiers; sweeteners; colorants; odorants; salts; buffers; coating agents; and antioxidants.

The compounds of the invention may be prepared as free acids or bases, which are then preferably combined with a suitable compound to yield a pharmaceutically acceptable salt. The expression "pharmaceutically acceptable salts" refers to non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like. Salts also include those from inorganic bases, such as ammonia, hydroxyethylamine and hydrazine. Suitable organic bases include methylamine, ethylamine, propylamine, dimethylamine, diethylamine, trimethylamine, triethylamine, ethylenediamine, hydroxyethylamine, morpholine, piperazine, and guanidine.

In this regard, the compounds, and their respective acid or base salts, can be formulated into liquid, preferably aqueous, formulations for storage and administration, as well as dried formulations that may, for example, be used as powders for intranasal administration or be reconstituted into liquid form just prior to administration to a subject. Liquid pharmaceutically administrable compositions can, for example, be prepared by dissolving, dispersing, etc. the particular active compound and optional pharmaceutical adjuvants in an aqueous carrier. Aqueous carriers include water (particularly water for injection into humans), alcoholic/aqueous solutions, and emulsions and suspensions. Preferred pharmaceutically acceptable aqueous carriers include sterile buffered isotonic saline solutions. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, and inert gases and the like. Non-aqueous solvents may also be included, although when included they preferably comprise less than about 50%, more preferably less than about 25%, and even more preferably less about 10%, of the total solvent of the solution. Examples of non-aqueous solvents include propylene glycol, ethanol, polyethylene glycol, vegetable oils such as olive oil, and injectable organic esters such as ethyl oleate. The pharmaceutical and veterinary compositions of the invention, whether dry or liquid, are preferably formulated for intranasal administration.

If desired, the composition to be administered may also contain minor amounts of nontoxic auxiliary substances such as wetting agents, emulsifying agents, or solubilizing agents, antioxidants, antimicrobials, pH buffering agents and the like, for example, sodium acetate, sodium citrate, cyclodextrin derivatives, sorbitan monolaurate, triethanolamine acetate, triethanolamine oleate, etc. Actual methods of preparing such dosage forms are known, or will be apparent, to those skilled in this art; for example, see Remington: The Science and Practice of Pharmacy, Mack Publishing Company, Easton, Pa., 20th Edition, 2000. The composition or formulation to be administered will, in any event, contain a quantity of the active compound in an amount effective to alleviate the symptoms of the subject being treated.

As those in the art will appreciate, the compounds of the invention may also be formulated for targeted delivery of the active ingredient to a subset of tissues or cells in a subject. In general, targeted delivery is accomplished by formulating a compound of the invention with a targeting moiety. Such moieties include lipids, liposomes, nanoparticles, and ligands for molecules that bind, or are bound by, other molecules in vivo. Examples of targeting moieties that can be used to target liposomes, nanoparticles, and the like include monoclonal antibodies that specifically bind to proteins or other biomolecules present on the exterior surface of cell membranes, particularly biomolecular targets that are preferentially expressed on the surface of diseased cells (e.g., cancer cells, pathogen-infected cells, etc.). As an example, folate-tethered nanoparticles loaded with a compound of the invention can be used to target activated macrophages, as such macrophages engulf tubercular bacilli and highly express folate receptors on their cell membranes.

A composition is comprised of "substantially all" of a particular compound, or a particular form a compound (e.g., an isomer) when a composition comprises at least about 90%, and preferably at least about 95%, 99%, and 99.9%, of the particular composition on a weight basis. A composition comprises a "mixture" of compounds, or forms of the same compound, when each compound (e.g., isomer) represents at least about 10% of the composition on a weight basis. A hyrdazone derivative of the invention, or a conjugate thereof, can be prepared as an acid salt or as a base salt, as well as in free acid or free base forms. In solution, certain of the compounds of the invention may exist as zwitterions, wherein counter ions are provided by the solvent molecules themselves, or from other ions dissolved or suspended in the solvent.

Generally, the concentration of a compound of the invention in a liquid composition, such as a lotion, will be from about 0.1-25% by weight of the composition, preferably from about 0.5-10% by weight. The concentration in a semi-solid or solid composition such as a gel or a powder typically is about 0.1-5% by weight, preferably about 0.5-2.5% by weight.

The amount of the compound required for use in treatment will vary not only with the particular compound and salt selected, but also with the route of administration, the nature of the condition being treated, and the age and condition of the patient, among other factors, and ultimately is determined at the discretion of the attending physician or clinician. The desired dose may conveniently be presented in a single dose or as divided doses administered at appropriate intervals, for example, as two, three, four or more sub-doses per day. The sub-dose itself may be further divided, for example, into a number of discrete, loosely spaced administrations, such as multiple inhalations from an insufflator or by application of a plurality of drops into the eye.

Administration

The compounds of this invention are administered in a therapeutically effective amount to a subject in need of treatment. Administration of the compositions of the invention can be via any of suitable route of administration, particularly parenterally, for example, intravenously, intra-arterially, intraperitoneally, intrathecally, intraventricularly, intraurethrally, intrasternally, intracranially, intramuscularly, intranasally, rectally, subcutaneously, sublingually, transdermally, or by inhalation or insufflation. Such administration may be as a single bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives. The preparation of suitable, and preferably sterile, parenteral formulations is described in detail in the section entitled "Compositions", above.

In the context of this invention, actual dosage levels for the compositions of this invention can be varied so as to obtain an amount of the active compound(s) that is effective to achieve the desired therapeutic response for a particular patient, compositions and mode of administration. In general, daily administration or continuous infusion at dosages less than those known to produce toxicities will be the preferred therapeutic protocol to enhance the activity of the drug. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

With regard to human and veterinary treatment, the amount of a particular composition that is administered will, of course, be dependent on a variety of factors, including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; the judgment of the prescribing physician or veterinarian; and like factors well known in the medical and veterinary arts.

The term "effective amount" of a compound (or composition, or the like) means an amount that is effective to exhibit the desired biological activity or achieve the desired clinical result in a subject response to the particular treatment, commensurate with a reasonable benefit/risk ratio when used in the manner of this invention.

A "therapeutically effective amount" refers to an amount of an active ingredient sufficient to effect treatment when administered to a subject in need of such treatment. In the context of cancer treatment, a "therapeutically effective amount" is one that produces an objective response in evaluable patients. Such responses include changes in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc., as well as the cessation or regression in growth determined against clinically accepted standards. With reference to these standards, determination of therapeutically effective dosages of a composition comprising a hydrazone derivative according to the invention may be readily made by those of ordinary skill in the art. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy.

The term "treatment" or "treating" means any treatment of a disease or disorder, including preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "protection" thus includes "prophylaxis".

As used herein with respect to cancer or cancer cells, the term "inhibition" or "inhibit" includes both the reduction in cellular proliferation, blockage of cellular proliferation, or killing some or all of said cells, including, for example, by activating a cellular pathway (e.g., the ERK pathway) associated with an extrinsic or intrinsic apoptotic pathway. Thus, the term can be used in both the context of a prophylactic treatment to prevent development of cancer or as a treatment that will block, or slow the spread of established cancer or other disease or disorder.

As used herein "treating" includes (i) preventing a pathologic condition from occurring (e.g., prophylaxis) or symptoms related to the same; (ii) inhibiting the pathologic condition or arresting its development or symptoms related to the same; and (iii) relieving the pathologic condition or symptoms related to the same.

As used herein "in combination with" or "administered in conjunction with" includes simultaneous administration, separate administration or sequential administration of at least two active agents in a manner that allows the desired beneficial effect to occur.

The magnitude of a prophylactic or therapeutic dose of a compound or compounds of formula (I) in the acute or chronic management of cancer, e.g., prostate cancer, will vary with the type and/or stage of the cancer, the adjunct chemotherapeutic agent(s) or other anti-cancer therapy used, and the route of administration. The dose, and perhaps the dose frequency, will also vary according to the age, body weight, condition, and response of the individual patient. In general, the total daily dose range for a compound or compounds of formula (I), for the conditions described herein, is from about 50 mg to about 5000 mg, in single or divided doses. Preferably, a daily dose range should be about 100 mg to about 4000 mg, most preferably about 1000-3000 mg, in single or divided doses, e.g., 750 mg every 6 hr of orally administered compound. This can achieve plasma levels of about 500-750 uM, which can be effective to kill cancer cells. In managing the patient, the therapy should be initiated at a lower dose and increased depending on the patient's global response.

Any suitable route of administration may be employed for providing the patient with an effective dosage of a compound of formula (I). For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The compound may be administered prior to, concurrently with, or after administration of chemotherapy, or continuously, i.e., in daily doses, during all or part of, a chemotherapy regimen. The compound, in some cases, may be combined with the same carrier or vehicle used to deliver the anti-cancer chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. Tablets, capsules, pills, granules, microparticles and the like can also comprise an enteric coating, such as a coating of one of the Eudragit® polymers, that will permit release of the active compound(s) in the intestines, not in the acidic environment of the stomach.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds may be applied in liquid or cream-based formulations, which preferably will include a dermatologically acceptable carrier, which may be a solid, gel, or liquid. Useful solid carriers include finely divided solids such as talc, clay, microcrystalline cellulose, silica, alumina and the like. Useful liquid carriers include water, alcohols, or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses, and/or modified mineral materials can also be employed with liquid carriers to form spreadable pastes, gels, ointments, soaps, and the like, for application directly to the skin of the user.

Useful dosages of the compounds of the invention can be determined by comparing their in vitro activity, and in vivo activity in animal models. Methods for the extrapolation of effective dosages in mice, and other animals, to humans are known to the art. See, e.g., U.S. Pat. No. 4,938,949.

Other drugs or treatments, including treatment with other chemotherapeutic agents, irradiation, or other anti-cancer agents such as alkylating agents, anti-tumor antibodies, or cytokines, can be used with the present compounds. See, e.g., Remington's Pharmaceutical Sciences (18$^{th}$ ed. 1990) at pages 1138-1162.

Applications

As described above, certain aspects of the invention relate to compositions that contain a compound of the invention, which compositions are useful in the treatment or prevention of a disease or disorder in, for example, humans or other mammals (e.g., bovine, canine, equine, feline, ovine, and porcine animals), and perhaps other animals as well. Specifically, this invention enables the treatment of cells, e.g., cancer cells, with the compounds of the invention, particularly solid tumors, leukemias, and other types of cancer. Examples include cancers such as breast, cervical, colorectal, and liver cancers, including breast adenocarcinoma, cervical adenocarcinoma, and hepatocellular carcinoma.

In the context of cancer, it is worth noting that a major obstacle to effective cancer therapy concerns the dose-limiting toxicity of many cytotoxic drugs, including the vinca alkaloids (e.g., vinblastine), the anthracyclines (e.g., doxorubicin), the epipodophyllotoxins (e.g., etoposide), the taxanes (e.g., taxol), antibiotics (e.g., actinomycin D), antimicrotubule drugs (e.g., colchicine), protein synthesis inhibitors (e.g., puromycin), toxic peptides (e.g., valinomycin), topoisomerase inhibitors (e.g., topotecan), DNA intercalators (e.g., ethidium bromide), and anti-mitotics.

In the context of cancer therapy, the compounds of the present invention may be used alone, i.e., in monotherapy, or in combination with other therapeutic agents or other anticancer therapies (e.g., radiation, surgery, bone marrow transplantation, etc.), as well as to potentiate the effects of other therapies, including treatment with other chemotherapeutic agents. As will be appreciated, "combination therapy" (in the context of cancer and other therapies) and the like refer to a course of therapy that involves the provision of at least two distinct therapies to achieve an indicated therapeutic effect. For example, a combination therapy may involve the administration of two or more chemically distinct active ingredients, for example, a fast-acting chemotherapeutic agent and a myeloprotective agent. The agents may be delivered or may be administered as part of the same composition or as different compositions according to the same therapeutic regimen or different regimens, depending on the active ingredients involved, the disease to be treated, the age and condition of the patient, etc. Moreover, when used in combination with another therapeutic agent, the administration of the two agents may be simultaneous or sequential. Simultaneous administration includes the administration of a single dosage form that comprises both agents, and the administration of the two agents in separate dosage forms at substantially the same time. Sequential administration includes the prior, concurrent, or subsequent administration of the two or more agents according to the same or different schedules, provided that there is an overlap in the periods during which the treatment is provided. Alternatively, a combination therapy may involve the administration of one or more chemotherapeutic agents as well as the delivery of radiation therapy and/or surgery or other techniques to either improve the quality of life of the patient or to treat the cancer. When one or more chemotherapeutic agents are combined with, for example, radiation and/or surgery, the drug(s) may be delivered before or after surgery or radiation treatment. Representative examples of other chemotherapeutic agents that can be used in combination with a compound according to the invention include Shikonin, Taxol, and Sorafenib.

EXAMPLES

The invention will be further described by reference to the following detailed examples. These Examples are in no way to be considered to limit the scope of the invention in any manner. Examples 1-23 describe chemical syntheses. Example 24 describes the pharmacological testing of several representative hydrazone derivatives of the invention.

Before turning to the specific examples, the general procedures used to prepare the described representative hydrazone derivatives employed a mixture of $N^6$-amino-adenosine or $N^6$-amino-9H-(3-C-methyl-β-D-ribofuranosyl)adenine, 6-hydrazinyl-9H-purine or 6-hydrazinyl-9-methyl-9H-purine (1.0 equiv.) and the appropriate carbonyl compound (1 equiv.) in methanol (10 mL) containing 5 to 10 drops glacial acetic acid was heated at 60 or 80° C., and the reaction was monitored by TLC ($CHCl_3$/MeOH 9:1). After completion, the reaction mixture was placed at 4° C. overnight. The obtained precipitates were filtered and recrystallized. Where there was no precipitate formed, the reaction mixture was evaporated to dryness and the compounds were recrystallized from the appropriate solvents or purified by chromatography.

Example 1

(2R,3S,5R)-2-(hydroxymethyl)-3-methyl-5-(6-(2-(phenyl(pyridin-2-yl)methylene)hydrazinyl)-9H-purin-9-yl)tetrahydrofuran-3,4-diol (I-1)

Starting material: $N^6$-Amino-9H-(3-C-methyl-β-D-ribofuranosyl)adenine: 100 mg; 0.337 mmol.
Reagent: 2-benzoyl-pyridine 68 mg; 0.337 mmol.
Reaction was complete after 3 h. The reaction mixture was evaporated to dryness and the residue was obtained as a light yellow solid (73%) after a preparative thin layer chromatography eluting with 5% MeOH/$CHCl_3$.
$^1$H NMR (DMSO-$d_6$, 400 MHz): Δ1.21 (s, 3H, $CH_3$), 3.56 (m, 1H, H-5'), 3.62 (m, 1H, H-5'), 3.91 (pseudo t, J=4.2 Hz, 1H, H-4'), 4.46 (t, J=7.1 Hz, 1H, H-2'), 4.89 (s, 1H, OH), 5.47 (d, J=6.8 Hz, 1H, OH), 5.57 (m, 1H, OH), 5.93 (d, J=7.7 Hz, 1H, H-1'), 7.41 (d, J=8.1 Hz, 1H, Pyr-H-4), 7.49 (m, 3H, Ar—H), 7.62 (m, 3H, Pyr-H-5, 2×Ar—H), 8.05 (m, 1H, Py-H-3), 8.44 (s, 1H, H-2), 8.59 (s, 1H, H-8), 8.92 (d, J=3.8 Hz, 1H, Pyr-H-6), 13.98 (br s, 1H, NH [Z]).
MS (API-ESI): m/z 461.1 $(M+H)^+$. Anal. calcd. for $C_{23}H_{23}N_7O_4$: C, 59.86; H, 5.02; N, 21.25. Found: C, 59.69; H, 5.09; N, 21.41.

Example 2

(2R,3S,4R)-2-(hydroxymethyl)-3-methyl-5-(6-(2-(1-(pyridin-2-yl)ethylidene)hydrazinyl)-9H-purin-9-yl)tetrahydrofuran-3,4-diol (I-2)

Starting material: $N^6$-Amino-9H-(3-C-methyl-β-D-ribofuranosyl)adenine 150 mg; 0.531 mmol.
Reagent: 4-acetyl-pyridine 45.9 mg; 0.531 mmol.
Reaction was complete after 4 h. The product precipitated out of the hot solution as the reaction proceeded. After cooling, the product was filtered and recrystallized from EtOH to give light yellow crystals (93%).
$^1$H NMR (DMSO-$d_6$, 400 MHz): Δ1.24 (s, 3H, $CH_3$), 2.51 (s, 3H, $CH_3$), 3.52 (m, 1H, H-5'), 3.64 (m, 1H, H-5'), 3.83 (t, J=2.9 Hz, 1H, H-4'), 4.41 (d, J=7.7 Hz, 1H, H-2'), 4.91 (br s, 1H, OH), 5.45 (br s, 2H, OH), 5.96 (d, J=7.7 Hz, 1H, H-1'), 7.61 (t, J=6.2 Hz, 1H, Pyr-H-5), 8.12 (t, J=8.1 Hz, 1H, Pyr-H-4), 8.45 (s, 1H, H-2), 8.51 (d, J=8.1 Hz, 1H, Py-H-3), 8.71 (s, 1H, H-8), 8.74 (br s, 1H, Pyr-H-6), 10.75 (br s, 1H, NH [E]).
MS (API-ESI): m/z 400.1 $(M+H)^+$. Anal. calcd. for $C_{18}H_{21}N_7O_4$: C, 54.13; H, 5.30; N, 24.55. Found: C, 54.27; H, 5.16; N, 24.67.

Example 3

(2R,3S,4R)-2-(hydroxymethyl)-3-methyl-5-(6-(2-(1-(pyridin-3-yl)ethylidene)hydrazinyl)-9H-purin-9-yl)tetrahydrofuran-3,4-diol (I-3)

Starting material: $N^6$-Amino-9H-(3-C-methyl-β-D-ribofuranosyl)adenine 120 mg; 0.425 mmol.
Reagent: 3-acetyl-pyridine 51.9 mg; 0.425 mmol.
Reaction was complete after 6 h. The product precipitated out of the hot solution as the reaction proceeded. After cooling, the product was filtered and recrystallized from EtOH to give yellow crystals (73%).

¹H NMR (DMSO-d$_6$, 400 MHz): Δ1.23 (s, 3H, CH$_3$), 2.44 (s, 3H, CH$_3$), 3.55 (m, 1H, H-5'), 3.68 (m, 1H, H-5'), 3.88 (t, J=2.8 Hz, 1H, H-4'), 4.42 (d, J=8.1 Hz, 1H, H-2'), 5.38 (br s, 1H, OH), 5.51 (br s, 2H, OH), 5.95 (d, J=8.1 Hz, 1H, H-1'), 7.86 (t, J=6.6 Hz, 1H, Pyr-H-5), 8.43 (s, 1H, H-2), 8.68 (s, 1H, H-8), 8.75 (d, J=5.1 Hz, 1H, Pyr-H-4), 8.84 (br s, 1H, Py-H-6), 9.41 (s, 1H, Py-H-2), 12.33 (br s, 1H, NH [E]).

MS (API-ESI): m/z 400.4 (M+H)$^+$. Anal. calcd. for C$_{18}$H$_{21}$N$_7$O$_4$: C, 54.13; H, 5.30; N, 24.55. Found: C, 54.03; H, 5.52; N, 24.28.

Example 4

(2R,3S,4R)-2-(hydroxymethyl)-3-methyl-5-(6-(2-(pyridin-2-yl)methylene)hydrazinyl)-9H-purin-9-yl)tetrahydrofuran-3,4-diol (I-4)

Starting material: N$^6$-Amino-9H-(3-C-methyl-β-D-ribofuranosyl)adenine 180 mg; 0.607 mmol.

Reagent: pyridine 2-carboxaldehyde 65.7 mg; 0.607 mmol.

Reaction was complete after 6 h. The product precipitated out of the hot solution as the reaction proceeded. After cooling, the product was filtered and recrystallized from EtOH to give yellow crystals (68%).

¹H NMR (DMSO-d$_6$, 400 MHz): Δ1.24 (s, 3H, CH$_3$), 3.56 (m, 1H, H-5'), 3.64 (m, 1H, H-5'), 3.97 (t, J=3.0 Hz, 1H, H-4'), 4.43 (d, J=7.7 Hz, 1H, H-2'), 5.21 (br s, 1H, OH), 5.33 (br s, 2H, OH), 5.92 (d, J=8.1 Hz, 1H, H-1'), 7.36 (dd, J=5.1, 6.3 Hz, 1H, Pyr-H-5), 8.03 (t, J=7.2 Hz, 1H, Pyr-H-4), 8.27 (d, J=8.1 Hz, 1H, Py-H-3), 8.51 (s, 1H, CH=N), 8.57 (s, 1H, H-2), 8.61 (d, J=5.1 Hz, 1H, Pyr-H-6), 8.73 (s, 1H, H-8), 11.94 (br s, 1H, NH [E]).

MS (API-ESI): m/z 386.2 (M+H)$^+$. Anal. calcd. for C$_{17}$H$_{19}$N$_7$O$_4$: C, 52.98; H, 4.97; N, 25.44. Found: C, 53.07; H, 4.76; N, 25.65.

Example 5

(2R,5R)-2-(hydroxymethyl)-5-(6-(2-(phenyl(pyridin-2-yl)methylene)hydrazinyl)-9H-purin-9-yl)tetrahydrofuran-3,4-diol (I-5)

Starting material: N$^6$-amino-adenosine 150 mg; 0.530 mmol.

Reagent: 2-benzoyl-pyridine 98 mg; 0.530 mmol.

Reaction was complete after 2 h. The reaction mixture was evaporated to dryness and the residue was purified by silica gel column chromatography eluting with a linear gradient (0-10% MeOH/CHCl$_3$) to give the final compound as a light yellow solid (75%).

¹H NMR (DMSO-d$_6$, 400 MHz): Δ3.57 (m, 1H, H-5'), 3.68 (m, 1H, H-5'), 3.96 (q, J=3.6, 7.0 Hz, 1H, H-4'), 4.16 (t, J=4.1 Hz, 1H, H-3'), 4.61 (t, J=5.4 Hz, 1H, H-2'), 5.28 (m, 2H, OH), 5.31 (br s, 1H, OH), 5.97 (d, J=6.9 Hz, 1H, H-1'), 7.42 (d, J=8.1 Hz, 1H, Pyr-H-4), 7.48 (m, 3H, Ar—H), 7.64 (m, 3H, Pyr-H-5, 2×Ar—H), 8.04 (dt, J=1.7, 7.9 Hz, 1H, Pyr-H-3), 8.48 (s, 1H, H-2), 8.61 (s, 1H, H-8), 8.93 (d, J=4.7 Hz, 1H, Pyr-H-6), 14.01 (br s, 1H, NH [Z]). MS (API-ESI): m/z 448.1 (M+H)$^+$. Anal. calcd. for C$_{22}$H$_{21}$N$_7$O$_4$: C, 59.05; H, 4.73; N, 21.91. Found: C, 59.15; H, 4.53; N, 21.73.

Example 6

(2R,5R)-2-(hydroxymethyl)-5-(6-(2-(1-(pyridin-2-yl)ethylidene)hydrazinyl)-9H-purin-9-yl)tetrahydrofuran-3,4-diol (I-6)

Starting material: N$^6$-amino-adenosine 120 mg; 0.424 mmol

Reagent: 2-acetyl-pyridine 52 mg; 0.424 mmol

Reaction was complete after 3 h. The product precipitated out of the hot solution as the reaction proceeded. After cooling, the product was filtered and recrystallized from MeOH to give light yellow crystals (79%).

¹H NMR (DMSO-d$_6$, 400 MHz): Δ2.42 (s, 3H, CH$_3$), 3.57 (m, 1H, H-5'), 3.68 (m, 1H, H-5'), 3.96 (d, J=3.4 Hz, 1H, H-4'), 4.18 (q, J=3.8 Hz, 1H, H-3'), 4.59 (q, J=5.3 Hz, 1H, H-2'), 5.21 (d, J=4.7 Hz, 1H, OH), 5.27 (t, J=5.5 Hz, 1H, OH), 5.48 (d, J=5.9 Hz, 1H, OH), 5.98 (d, J=5.9 Hz, 1H, H-1'), 7.35 (t, J=5.9 Hz, 1H, Pyr-H-5), 7.85 (t, J=7.5 Hz, 1H, Pyr-H-4), 8.42 (s, 1H, H-2), 8.52 (d, J=8.1 Hz, 1H, Pyr-H-3), 8.57 (d, J=4.3 Hz, 1H, Pyr-H-6), 8.61 (s, 1H, H-8), 10.82 (br s, 1H, NH [E]).

MS (API-ESI): m/z 386.1 (M+H)$^+$. Anal. calcd. for C$_{17}$H$_{19}$N$_7$O$_4$: C, 52.98; H, 4.97; N, 25.44. Found: C, 52.77; H, 5.06; N, 25.51.

Example 7

(2R,5R)-2-(hydroxymethyl)-5-(6-(2-(1-(pyridin-3-yl)ethylidene)hydrazinyl)-9H-purin-9-yl)tetrahydrofuran-3,4-diol (I-7)

Starting material: N$^6$-amino-adenosine 120 mg; 0.425 mmol

Reagent: 3-acetyl-pyridine 51.9 mg; 0.425 mmol

Reaction was complete after 4 h. The product precipitated out of the hot solution as the reaction proceeded. After cooling, the product was filtered and recrystallized from MeOH to give light yellow crystals (75%).

¹H NMR (DMSO-d$_6$, 400 MHz): Δ2.41 (s, 3H, CH$_3$), 3.57 (m, 1H, H-5'), 3.67 (m, 1H, H-5'), 3.96 (q, J=3.6 Hz, 1H, H-4'), 4.16 (q, J=4.5 Hz, 1H, H-3'), 4.58 (q, J=5.5 Hz, 1H, H-2'), 5.22 (d, J=4.7 Hz, 1H, OH), 5.24 (t, J=5.5 Hz, 1H, OH), 5.49 (d, J=5.9 Hz, 1H, OH), 5.97 (d, J=5.9 Hz, 1H, H-1'), 7.45 (dd, J=4.9, 7.9 Hz, 1H, Pyr-H-5), 8.28 (m, 1H, Pyr-H-4), 8.41 (s, 1H, H-2), 8.55 (dd, J=1.7, 4.7 Hz, 1H, Pyr-H-6), 8.59 (s, 1H, H-8), 9.21 (d, J=2.1 Hz, 1H, Pyr-H-2), 10.84 (br s, 1H, NH [E]).

MS (API-ESI): m/z 386.1 (M+H)$^+$. Anal. calcd. for C$_{17}$H$_{19}$N$_7$O$_4$: C, 52.98; H, 4.97; N, 25.44. Found: C, 53.06; H, 5.02; N, 25.21.

Example 8

(2R,5R)-2-(hydroxymethyl)-5-(6-(2-(1-(pyridin-4-yl)ethylidene)hydrazinyl)-9H-purin-9-yl)tetrahydrofuran-3,4-diol (I-8)

Starting material: N$^6$-amino-adenosine 160 mg; 0.566 mmol.

Reagent: 4-acetyl-pyridine 69.2 mg; 0.566 mmol.

Reaction was complete after 5 h. The product precipitated out of the hot solution as the reaction proceeded. After cooling, the product was filtered and recrystallized from MeOH to give light yellow crystals (90%).

¹H NMR (DMSO-d$_6$, 400 MHz): Δ2.23 (s, 3H, CH$_3$), 3.56 (m, 1H, H-5'), 3.68 (m, 1H, H-5'), 3.96 (pseudo d, J=3.4 Hz, 1H, H-4'), 4.18 (q, J=4.5 Hz, 1H, H-3'), 4.59 (q, J=5.6 Hz, 1H, H-2'), 5.21 (d, J=4.7 Hz, 1H, OH), 5.23 (t, J=5.6 Hz, 1H, OH), 5.48 (d, J=6.4 Hz, 1H, OH), 5.98 (d, J=5.5 Hz, 1H, H-1'), 7.97 (pseudo d, J=6.0 Hz, 2H, Pyr-H-3, Pyr-H-5), 8.43 (s, 1H, H-2), 8.61 (pseudo d, J=6.5 Hz, 2H, Pyr-H-2, Py-H-6), 8.63 (s, 1H, H-8), 10.88 (br s, 1H, NH [E]).

MS (API-ESI): m/z 386.1 (M+H)$^+$. Anal. calcd. for C$_{17}$H$_{19}$N$_7$O$_4$: C, 52.98; H, 4.97; N, 25.44. Found: C, 53.18; H, 5.09; N, 25.18.

Example 9

(2R,3S,4R)-2-(hydroxymethyl)-5-(6-(2-(pyridin-2-yl)methylene)hydrazinyl)-9H-purin-9-yl)tetrahydrofuran-3,4-diol (I-9)

Starting material: N$^6$-amino-adenosine 150 mg; 0.531 mmol.

Reagent: pyridine 2-carboxyaldehyde 57.4 mg; 0.531 mmol.

Reaction was complete after 5 h. The product precipitated out of the hot solution as the reaction proceeded. After cooling, the product was filtered and recrystallized from MeOH to give light yellow crystals (95%).

$^1$H NMR (DMSO-d$_6$, 400 MHz): Δ3.58 (m, 1H, H-5'), 3.71 (m, 1H, H-5'), 3.92 (pseudo q, J=3.5 Hz, 1H, H-4'), 4.17 (q, J=4.5 Hz, 1H, H-3'), 4.62 (q, J=5.9 Hz, 1H, H-2'), 5.18 (d, J=4.7 Hz, 1H, OH), 5.26 (t, J=5.6 Hz, 1H, OH), 5.51 (d, J=5.9 Hz, 1H, OH), 5.99 (d, J=5.9 Hz, 1H, H-1'), 7.36 (dd, J=5.5, 6.8 Hz, 1H, Pyr-H-5), 7.83 (t, J=7.3 Hz, 1H, Pyr-H-4), 8.06 (d, J=8.1 Hz, 1H, Pyr-H-3), 8.37 (s, 1H, H-2), 8.42 (s, 1H, H-8), 8.61 (br s, 1H, Pyr-H-6), 8.63 (s, 1H, CH=N), 12.04 (br s, 1H, NH [E]).

MS (API-ESI): m/z 372.2 (M+H)$^+$. Anal. calcd. for C$_{16}$H$_{17}$N$_7$O$_4$: C, 51.75; H, 4.61; N, 26.40. Found: C, 51.93; H, 4.46; N, 26.53.

Example 10

(2R,3S,4R)-2-(hydroxymethyl)-5-(6-(2-(pyridin-3-yl)methylene)hydrazinyl)-9H-purin-9-yl)tetrahydrofuran-3,4-diol (I-10)

Starting material: N$^6$-amino-adenosine 200 mg; 0.708 mmol.

Reagent: pyridine 3-carboxyaldehyde 76.8 mg; 0.708 mmol.

Reaction was complete after 5 h. The product precipitated out of the hot solution as the reaction proceeded. After cooling, the product was filtered and recrystallized from MeOH to give light yellow crystals (81%).

$^1$H NMR (DMSO-d$_6$, 400 MHz): Δ3.58 (m, 1H, H-5'), 3.68 (m, 1H, H-5'), 3.95 (q, J=3.7 Hz, 1H, H-4'), 4.14 (q, J=4.9 Hz, 1H, H-3'), 4.61 (q, J=5.7 Hz, 1H, H-2'), 5.20 (d, J=4.7 Hz, 1H, OH), 5.26 (t, J=4.9 Hz, 1H, OH), 5.48 (d, J=5.9 Hz, 1H, OH), 5.96 (d, J=5.9 Hz, 1H, H-1'), 7.47 (dd, J=4.9, 7.9 Hz, 1H, Pyr-H-5), 8.16 (dt, J=1.7, 8.1 Hz, 1H, Pyr-H-4), 8.37 (s, 1H, CH=N), 8.40 (s, 1H, H-2), 8.55 (s, 1H, H-8), 8.58 (dd, J=1.7, 4.2 Hz, 1H, Pyr-H-6), 8.87 (d, J=2.1 Hz, 1H, Pyr-H-2), 11.96 (br s, 1H, NH [E]).

MS (API-ESI): m/z 372.2 (M+H)$^+$. Anal. calcd. for C$_{16}$H$_{17}$N$_7$O$_4$: C, 51.75; H, 4.61; N, 26.40. Found: C, 51.84; H, 4.52; N, 26.46.

Example 11

(2R,3S,4R)-2-(hydroxymethyl)-5-(6-(2-(pyridin-4-yl)methylene)hydrazinyl)-9H-purin-9-yl)tetrahydrofuran-3,4-diol (I-11)

Starting material: N$^6$-amino-adenosine 90 mg; 0.318 mmol.

Reagent: pyridine 4-carboxyaldehyde 34.5 mg; 0.318 mmol.

Reaction was complete after 5 h. The product precipitated out of the hot solution as the reaction proceeded. After cooling, the product was filtered and recrystallized from MeOH to give yellow crystals (80%).

$^1$H NMR (DMSO-d$_6$, 400 MHz): Δ3.56 (m, 1H, H-5'), 3.67 (m, 1H, H-5'), 3.96 (q, J=3.4 Hz, 1H, H-4'), 4.16 (q, J=4.9 Hz, 1H, H-3'), 4.61 (q, J=5.9 Hz, 1H, H-2'), 5.22 (d, J=4.7 Hz, 1H, OH), 5.33 (q, J=5.1 Hz, 1H, OH), 5.49 (d, J=6.4 Hz, 1H, OH), 5.96 (d, J=5.9 Hz, 1H, H-1'), 7.68 (pseudo d, J=5.9 Hz, 2H, Pyr-H-3, Pyr-H-5), 8.29 (s, 1H, CH=N), 8.42 (s, 1H, H-2), 8.58 (s, 1H, H-8), 8.61 (pseudo d, J=5.9 Hz, 2H, Pyr-H-2, Pyr-H-6), 12.11 (br s, 1H, NH [E]).

MS (API-ESI): m/z 372.2 (M+H)$^+$. Anal. calcd. for C$_{16}$H$_{17}$N$_7$O$_4$: C, 51.75; H, 4.61; N, 26.40. Found: C, 51.62; H, 4.70; N, 26.43.

Example 12

(2R,3S,4R)-2-(hydroxymethyl)-5-(6-(2-(propan-2-ylidene)hydrazinyl)-9H-purin-9-yl)tetrahydrofuran-3,4-diol (I-12)

Starting material: N$^6$-amino-adenosine 90 mg; 0.318 mmol.

Reagent: acetone 18.2 mg; 0.318 mmol.

Reaction was complete after 5 h. The reaction mixture was evaporated to dryness and the residue was purified by silica gel column chromatography eluting with a linear gradient (0-10% MeOH/CHCl$_3$) to give the final compound as a white solid (76%).

$^1$H NMR (DMSO-d$_6$, 400 MHz): Δ1.96 (s, 3H, CH$_3$), 2.03 (s, 1H, CH$_3$), 3.57 (dd, J=3.4, 11.9 Hz, 1H, H-5'), 3.64 (dd, J=3.8, 11.9 Hz, 1H, H-5'), 3.95 (q, J=3.6 Hz, 1H, H-4'), 4.14 (t, J=4.7 Hz, 1H, H-3'), 4.36 (br s, 1H, NH), 4.58 (d, J=5.7 Hz, 1H, H-2'), 5.21 (br s, 1H, OH), 5.32 (br s, 1H, OH), 5.48 (br s, 1H, OH), 5.92 (d, J=6.0 Hz, 1H, H-1'), 8.27 (s, 1H, H-2), 8.33 (s, 1H, H-8).

MS (API-ESI): m/z 323.1 (M+H)$^+$. Anal. calcd. for C$_{13}$H$_{18}$N$_6$O$_4$: C, 48.44; H, 5.63; N, 26.07. Found: C, 48.62; H, 5.71; N, 26.01.

Example 13

(3R,4S,5R)-2-(6-(2-(dipyridin-2-yl)methylene)hydrazinyl)-9H-purin-9-yl)-5-(hydroxymethyl)tetrahydrofuran-3,4-diol (I-13)

Starting material: N$^6$-amino-adenosine 180 mg; 0.566 mmol

Reagent: dipyridil ketone 105.4 mg; 0.566 mmol

Reaction was complete after 4 h. The product precipitated out of the hot solution as the reaction proceeded. After cooling, the product was filtered and recrystallized from MeOH to give yellowish crystals (78%).

$^1$H NMR (DMSO-d$_6$, 400 MHz): Δ3.56 (m, 1H, H-5'), 3.68 (m, 1H, H-5'), 3.92 (pseudo q, J=3.4 Hz, 1H, H-4'), 4.16 (q, J=4.5 Hz, 1H, H-3'), 4.61 (q, J=5.5 Hz, 1H, H-2'), 5.24 (m, 2H, OH), 5.52 (d, J=5.9 Hz, 1H, OH), 5.98 (d, J=5.6 Hz, 1H, H-1'), 7.47 (m, 1H, Pyr-H-5), 7.62 (m, 1H, Pyr-H-4), 7.98 (q, J=8.3 Hz, 1H, Pyr-H-3), 8.49 (s, 1H, H-2), 8.64 (s, 1H, H-8), 8.88 (d, J=4.7 Hz, 1H, Pyr-H-6), 14.24 (br s, 1H, NH).

MS (API-ESI): m/z 449.2 (M+H)$^+$. Anal. calcd. for C$_{21}$H$_{19}$N$_8$O$_4$: C, 56.25; H, 4.50; N, 24.99. Found: C, 56.17; H, 4.66; N, 25.05.

Example 14

2-((2-(9-((3R,4S,5R)-3,4-dihydroxy-5-(hydroxymethyl)tetrahydrofuran-2-yl)-9H-purin-6-yl)hydrazono)methyl)benzonitrile (I-14)

Starting material: $N^6$-amino-adenosine 120 mg; 0.424 mmol.

Reagent: 2-cyano-carboxyaldehyde 56 mg; 0.424 mmol.

Reaction was complete after 6 h at 60° C. The product precipitated out of the hot solution as the reaction proceeded. After cooling, the product was filtered and recrystallized from MeOH to give white crystals (85%).

$^1$H NMR (DMSO-$d_6$, 400 MHz): Δ3.63 (m, 1H, H-5'), 3.77 (m, 1H, H-5'), 3.95 (br s, 1H, H-4'), 4.17 (t, J=4.5 Hz, 1H, H-3'), 4.60 (d, J=5.5 Hz, 1H, H-2'), 5.23 (m, 2H, OH), 5.49 (d, J=5.6 Hz, 1H, OH), 5.98 (d, J=4.6 Hz, 1H, H-1'), 7.54 (t, J=7.5 Hz, 1H, Ar—H-5), 7.72 (t, J=7.2 Hz, 1H, Ar—H-4), 7.82 (d, J=7.7 Hz, 1H, Ar—H-3), 8.51 (d, J=8.1 Hz, 1H, Ar—H-6), 8.44 (s, 1H, H-2), 8.58 (s, 1H, H-8), 8.73 (s, 1H, CH=N), 12.21 (br s, 1H, NH [E]).

MS (API-ESI): m/z 396.3 (M+H)$^+$. Anal. calcd. for $C_{18}H_{17}N_7O_4$: C, 54.68; H, 4.33; N, 24.80. Found: C, 54.57; H, 4.40; N, 24.91.

Example 15

(2R,3S,4R)-2-(hydroxymethyl)-5-(6-(2-((5-methylthiophen-2-yl)methylene)hydrazinyl)-9H-purin-9-yl)tetrahydrofuran-3,4-diol (I-15)

Starting material: $N^6$-amino-adenosine 140 mg; 0.495 mmol.

Reagent: 5-methylthiophene-2-carbaldehyde 63.2 mg; 0.495 mmol.

Reaction was complete after 4 h. The product precipitated out of the hot solution as the reaction proceeded. After cooling, the product was filtered and recrystallized from MeOH to give a black solid (75%).

$^1$H NMR (DMSO-$d_6$, 400 MHz): Δ2.42 (s, 3H, CH$_3$), 3.56 (m, 1H, H-5'), 3.64 (m, 1H, H-5'), 3.93 (pseudo q, J=3.0 Hz, 1H, H-4'), 4.17 (q, J=4.5 Hz, 1H, H-3'), 4.59 (q, J=5.9 Hz, 1H, H-2'), 5.21 (d, J=4.7 Hz, 1H, OH), 5.32 (t, J=5.5 Hz, 1H, OH), 5.49 (d, J=6.4 Hz, 1H, OH), 5.94 (d, J=5.9 Hz, 1H, H-1'), 6.81 (d, J=2.5 Hz, 1H, Thiop-H-4), 7.15 (d, J=3.4 Hz, 1H, Thiop-H-3), 8.35 (s, 1H, CH=N), 8.43 (s, 1H, H-2), 8.49 (s, 1H, H-8), 11.65 (br s, 1H, NH [E]).

MS (API-ESI): m/z 391.1 (M+H)$^+$. Anal. calcd. for $C_{16}H_{18}N_6O_4S$: C, 49.22; H, 4.65; N, 21.53. Found: C, 49.36; H, 4.49; N, 21.38.

Example 16

(3R,4S,5R)-2-(6-(2-benzylidene)hydrazinyl)-9H-purin-9-yl)-5-(hydroxymethyl)tetrahydrofuran-3,4-diol (I-16)

Starting material: $N^6$-amino-adenosine 90 mg; 0.318 mmol.

Reagent: benzaldehyde 33.9 mg; 0.318 mmol.

Reaction was complete after 4 h. The product precipitated out of the hot solution as the reaction proceeded. After cooling, the product was filtered and recrystallized from MeOH to give white crystals (86%).

$^1$H NMR (DMSO-$d_6$, 400 MHz): Δ3.55 (dd, J=3.4, 11.9 Hz, 1H, H-5'), 3.67 (dd, J=3.8, 12.3 Hz, 1H, H-5'), 3.94 (q, J=3.6 Hz, 1H, H-4'), 4.18 (q, J=4.7 Hz, 1H, H-3'), 4.60 (q, J=5.7 Hz, 1H, H-2'), 5.22 (d, J=5.1 Hz, 1H, OH), 5.31 (t, J=5.5 Hz, 1H, OH), 5.47 (d, J=5.5 Hz, 1H, OH), 5.92 (d, J=5.5 Hz, 1H, H-1'), 7.41 (m, 3H, Ar—H), 7.75 (d, J=7.7 Hz, 2H, Ar—H), 8.32 (s, 1H, H-2), 8.39 (s, 1H, H-8), 8.52 (s, 1H, CH=N), 12.81 (br s, 1H, NH [E]).

MS (API-ESI): m/z 371.2 (M+H)$^+$. Anal. calcd. for $C_{17}H_{18}N_6O_4$: C, 55.13; H, 4.90; N, 22.69. Found: C, 55.20; H, 4.86; N, 22.75.

Example 17

(2R,3S,4R)-2-(hydroxymethyl)-5-(6-(2-(1-phenylethylidene)hydrazinyl)-9H-purin-9-yl)tetrahydrofuran-3,4-diol (I-17)

Starting material: $N^6$-amino-adenosine 90 mg; 0.318 mmol.

Reagent: acetophenone 38.4 mg; 0.318 mmol.

Reaction was complete after 3 h. The product precipitated out of the hot solution as the reaction proceeded. After cooling, the product was filtered and recrystallized from MeOH to give white crystals (77%).

$^1$H NMR (DMSO-$d_6$, 400 MHz): Δ2.38 (s, 3H, CH$_3$), 3.54 (m, 1H, H-5'), 3.66 (m, 1H, H-5'), 3.92 (q, J=3.7 Hz, 1H, H-4'), 4.16 (t, J=4.3 Hz, 1H, H-3'), 4.55 (br s, 1H, H-2'), 5.24 (br s, 2H, OH), 5.51 (br s, 1H, OH), 5.93 (d, J=5.9 Hz, 1H, H-1'), 7.42 (m, 3H, Ar—H), 8.03 (d, J=7.3 Hz, 2H, Ar—H), 8.34 (s, 1H, H-2), 8.51 (s, 1H, H-8), 10.63 (br s, 1H, NH [E]).

MS (API-ESI): m/z 371.2 (M+H)$^+$. Anal. calcd. for $C_{18}H_{20}N_6O_4$: C, 56.24; H, 5.24; N, 21.86. Found: C, 56.33; H, 5.16; N, 21.91.

Example 18

6-(2-(Pyridin-2-ylmethylene)hydrazinyl)-9H-purine (I-18)

Starting material: 6-hydrazinyl-9H-purine 120 mg; 0.799 mmol

Reagent: pyridine 2-carboxyaldehyde 86.4 mg; 0.799 mmol

Reaction was complete after 4 h. The reaction mixture was evaporated to dryness and the residue was purified by silica gel column chromatography eluting with a linear gradient (0-10% MeOH/CHCl$_3$) to give the final compound as a yellowish solid (75%).

$^1$H NMR (DMSO-$d_6$, 400 MHz)$^{TM}$: Δ7.37 (q, J=5.3 Hz, 1H, Pyr-H-5), 7.88 (dt, J=1.3, 7.7 Hz, 1H, Pyr-H-4), 8.33 (br s, 2H, Pyr-H-3, H-2), 8.39 (br s, 2H, H-8, CH=N), 8.58 (d, J=4.7 Hz, 1H, Pyr-H-6), 12.01 (br s, 1H, NH [E]), 13.21 (br s, 1H, NH).

MS (API-ESI): m/z 240.1 (M+H)$^+$. Anal. calcd. for $C_{11}H_9N_7$: C, 55.22; H, 3.79; N, 40.98. Found: C, 55.31; H, 3.66; N, 40.89.

Example 19

6-(2-(Phenyl(pyridin-2-yl)methylene)hydrazinyl)-9H-purine (I-19)

Starting material: 6-hydrazinyl-9H-purine 96 mg; 0.639 mmol.

Reagent: phenyl(pyridin-2-yl)methanone 118.3 mg; 0.639 mmol.

Reaction was complete after 5 h. The product precipitated out of the hot solution as the reaction proceeded. After cooling, the product was filtered and recrystallized from MeOH to give white crystals (71%).

$^1$H NMR (DMSO-$d_6$, 400 MHz): Δ7.39 (m, 3H, Ar—H), 7.48 (d, J=6.2 Hz, 1H, Pyr-H-5), 7.63 (m, 3H, Pyr-H-4, 2×Ar—H), 8.06 (m, 1H, Pyr-H-3), 8.43 (s, 1H, H-2), 8.57 (s, 1H, H-8), 8.81 (d, J=5.1 Hz, 1H, Pyr-H-6), 9.31 (br s, 1H, NH), 12.77 (br s, 1H, NH [E]).

MS (API-ESI): m/z 316.2 (M+H)$^+$. Anal. calcd. for $C_{17}H_{13}N_7$: C, 64.75; H, 4.16; N, 31.09. Found: C, 64.81; H, 4.06; N, 31.13.

Example 20

6-(2-(Dipyridin-2-ylmethylene)hydrazinyl)-9H-purine (I-20)

Starting material: 6-hydrazinyl-9H-purine 150 mg; 0.999 mmol.

Reagent: dipyridyl ketone 185.6 mg; 0.999 mmol.

Reaction was complete after 4 h. The product precipitated out of the hot solution as the reaction proceeded. After cooling, the product was filtered and recrystallized from MeOH to give white crystals (76%).

$^1$H NMR (DMSO-$d_6$, 400 MHz): Δ7.53 (q, J=4.7 Hz, 1H, Pyr-H-5), 7.93 (q, J=6.4 Hz, 1H, Pyr-H-4), 8.33 (s, 1H, H-2), 8.44 (s, 1H, H-8), 8.59 (br s, 1H, Pyr-H-3), 8.84 (d, J=4.2 Hz, 1H, Pyr-H-6), 11.91 (br s, 1H, NH), 13.20 (br s, 1H, NH).

MS (API-ESI): m/z 316.2 (M+H)$^+$. Anal. calcd. for $C_{16}H_{12}N_8$: C, 60.75; H, 3.82; N, 35.42. Found: C, 60.82; H, 3.76; N, 35.35.

Example 21

6-[2-((5-Methylthiophen-2-yl)methylene)hydrazinyl]-9H-purine (I-21)

Starting material: 6-hydrazinyl-9H-purine 100 mg; 0.664 mmol.

Reagent: 5-methylthiophene-2-carbaldehyde 84.8 mg; 0.664 mmol.

Reaction was complete after 4 h. The product precipitated out of the hot solution as the reaction proceeded. After cooling, the product was filtered and recrystallized from MeOH to give a yellow/orange solid (51%).

$^1$H NMR (DMSO-$d_6$, 400 MHz): Δ2.41 (s, 3H, $CH_3$), 7.12 (d, J=2.9 Hz, 1H, Thiop-H-4), 7.31 (d, J=3.4 Hz, 1H, Thiop-H-3), 8.21 (s, 1H, H-2), 8.28 (s, 1H, H-8), 8.43 (s, 1H, CH=N), 11.41 (br s, 1H, NH), 13.07 (br s, 1H, NH [E]).

MS (API-ESI): m/z 391.1 (M+H)$^+$. Anal. calcd. for $C_{11}H_{10}N_6S$: C, 51.15; H, 3.90; N, 32.54. Found: C, 51.23; H, 3.79; N, 32.48.

Example 22

6-(2-(1H-Pyrrol-2-yl)methylene)hydrazinyl)-9H-purine (I-22)

Starting material: 6-hydrazinyl-9H-purine 100 mg; 0.666 mmol.

Reagent: 1H-pyrrole-2-carbaldehyde 64 mg; 0.666 mmol.

Reaction was complete after 4 h. The product precipitated out of the hot solution as the reaction proceeded. After cooling, the product was filtered and recrystallized from MeOH to give a white solid (77%).

$^1$H NMR (DMSO-$d_6$, 400 MHz): Δ4.43 (br s, 1H, Pyrr-NH), 6.12 (q, J=2.7 Hz, 1H, Pyrr-H-4), 6.43 (q, J=3.8 Hz, 1H, Pyrr-H-5), 7.12 (pseudo q, J=2.7 Hz, 1H, Pyrr-H-3), 8.23 (s, 1H, H-2), 8.41 (s, 1H, H-8), 8.78 (s, 1H, CH=N), 11.42 (br s, 1H, NH), 12.93 (br s, 1H, NH [E]).

MS (API-ESI): m/z 360.2 (M+H)$^+$. Anal. calcd. for $C_{10}H_9N_7$: C, 52.86; H, 3.99; N, 43.15. Found: C, 52.78; H, 4.05; N, 43.26.

Example 23

6-(2-(Dipyridin-2-yl)methylene)hydrazinyl)-9-methyl-9H-purine (I-23)

Starting material: 6-hydrazinyl-9-methyl-9H-purine 120 mg; 0.730 mmol.

Reagent: dipyridyl ketone 135.7 mg; 0.730 mmol.

Reaction was complete after 4 h. The product precipitated out of the hot solution as the reaction proceeded. After cooling, the product was filtered and recrystallized from MeOH to give white crystals (78%).

$^1$H NMR (DMSO-$d_6$, 400 MHz): Δ3.44 (s, 3H, $CH_3$), 7.24 (br s, 2H, Pyr-H-5), 7.54 (d, J=5.5 Hz, 2H, Pyr-H-4), 7.96 (s, 1H, H-2), 8.04 (s, 1H, H-8), 8.51 (br s, 2H, Pyr-H-3), 8.74 (d, J=4.2 Hz, 2H, Pyr-H-6), 12.11 (br s, 1H, NH).

MS (API-ESI): m/z 316.2 (M+H)$^+$. Anal. calcd. for $C_{17}H_{142}N_8$: C, 61.81; H, 4.27; N, 33.92. Found: C, 61.89; H, 4.16; N, 33.98.

Example 24

The example describes pharmacological test results of certain hydrazone derivatives according to the invention, which results demonstrate antitumor activity.

Introduction

Despite new findings in tumor biology, surgical intervention, and irradiation, antitumor drugs continue to play major roles in tumor therapy. Disadvantages of the antitumor drugs available to date are serious side effects, low response rates in solid tumors, and the development of resistance. In particular, in colon and ovarian carcinoma, two of the most frequently occurring tumors in Western countries, chemotherapy shows only limited efficacy. Therefore, more effective antitumor substances are clearly needed.

The compounds of this invention have been designed starting from the observation that adenosine analogues that contain a structural motif able to inhibit the enzyme ribonucleotide reductase could have antiproliferative activity. As explained herein, the hydrazone derivative compounds described in this example were synthesized and tested against a panel of human tumor cell lines (leukemia and carcinoma) showing a potent antitumor activity. Selected compounds, tested at the National Cancer Institute (Bethesda, Md.), proved to be highly active against 60 human tumor cell lines representing leukemia, melanoma, and cancers of the lung, colon, brain, ovary, kidney, prostate, and breast. These compounds were found active also against tumor cell lines resistant to available antineoplastic drugs. The mechanism of action of these compounds appears to be different from those of known antitumor agents. As such, these and the other compounds of the invention represent an exciting new class of antineoplastic agents, as described in more detail below.

Inhibition of Tumor Cell Growth

In order to obtain information about the growth-inhibiting action of hydrazones reported in the present invention on tumor cells, growth inhibition was assessed for the following human tumor cell lines: human myelogenous leukemia K562, human cervical adenocarcinoma HeLa, human colon adenocarcinoma Caco-2, human colon carcinoma HT-29, human colon carcinoma HCT-15, and human breast carcinoma MCF-7.

The K562, HeLa, HT-29, HCT-15, Caco-2, and MCF-7 cell lines were obtained from the American type Culture Collection (ATCC, Manassas, Va.). K562 cells were maintained in RPMI 1640 medium (Gibco/Life Technologies, Gaithersburg, Md.) containing 10% heat-inactivated fetal bovine serum (FBS) (Atlanta Biologicals, Atlanta, Ga.) and 10000 U/L penicillin and 50 mg/L streptomycin. HeLa, HT-29, HCT-15, Caco-2 and MCF-7 cells were maintained in MEM with Earl's balanced salts, 10% FBS, penicillin, and streptomycin as above. Logarithmically growing HT-29, Caco-2, and MCF-7 cells were incubated with 0.05% trypsin containing 1 mM EDTA at 37° C. for about 5 min until cells were nonadherent and formed a single cell suspension. Trypsin activity was neutralized by adding 20-fold excess of the serum-containing medium. Cells were cultured at 37° C. in an atmosphere of air and 5% $CO_2$.

Cytotoxicity assays were conducted by tetrazolium reduction of 3-(4,5-dimethylthiazol-2-yl)-5-(3-carboxymethoxyphenyl)-2-(4-sulfophenyl)-2H-tetrazolium (MTS) with N-methylphenazonium methyl sulfate (PMS) (CellTiter Assay, Promega, Madison, Wis.). Logarithmically growing cells were plated in 0.1 mL aliquots in 96-well microtiter plates. Cells were plated at an initial density of about 5000 cells/mL and allowed to acclimatize for 24 h. Cell suspensions were treated with various dilutions of compounds in triplicate, mixed well, and allowed to incubate for 48 h at 37° C. in an atmosphere of air and 5% $CO_2$. To the cell suspension was added 20 µL of tetrazolium reagent, the mixture was incubated for 2 h at 37° C. in an atmosphere of air and 5% $CO_2$, and absorbance at 490 nm was read by microplate reader. Control plates with serial dilutions of cell types were counted as a control for the assay. In all cases, controls indicated a linear response versus cell number, $R^2 \geq 0.99$. The results are shown in Tables I-III As shown in Tables I-III, compounds of the present invention exhibit excellent in vitro anti-tumor activities ($GI_{50}$) against human cancer cells with $GI_{50}$ ranging from submicromolar to low micromolar values.

TABLE I

In vitro activity of compounds I against human tumor cell lines
Cytotoxicity $GI_{50}$ (µM)

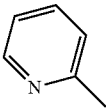

| Compd | R1 | R2 | Config. | K562 | HeLa | HT-29 | HCT-15 | Caco-2 | MCF-7 |
|---|---|---|---|---|---|---|---|---|---|
| RPC024 I-1 | 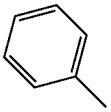 | 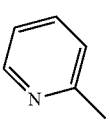 | Z | 48.1 | 68.9 | 57.2 | ND | 43.2 | >100 |
| RPC035 I-2 | 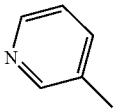 | CH₃ | E | 11.0 | 21.0 | 17.6 | ND | 23.0 | 13.5 |
| RPC048 I-3 | 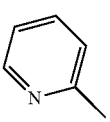 | CH₃ | E | 12.0 | 17.0 | 15.0 | 11.2 | 2.2 | 17.0 |
| RPC044 I-4 | 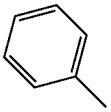 | H | E | 6.8 | 7.6 | 27.0 | 3.9 | 7.6 | 22.0 |

TABLE II

In vitro activity of compounds Ia against human tumor cell lines.
Cytotoxicity GI$_{50}$ (μM)

| Compd | R1 | R2 | Config | K562 | HeLa | HT-29 | HCT-15 | Caco-2 | MCF-7 |
|---|---|---|---|---|---|---|---|---|---|
| RPC023 I-5 | 2-pyridyl | phenyl | Z | 49.0 | 36.0 | 52.5 | ND | 64.5 | 44.9 |
| RPC032 I-6 | 2-pyridyl | CH$_3$ | E | 11.0 | 12.0 | 38.0 | ND | 14.0 | 15.0 |
| RPC033 I-7 | 3-pyridyl | CH$_3$ | E | 45.0 | 25.0 | 144.0 | ND | 63.3 | 93.0 |
| RPC034 I-8 | 4-pyridyl | CH$_3$ | E | 56.0 | 60.0 | 213.0 | ND | 49.6 | 68.0 |
| RPC038 I-9 | 2-pyridyl | H | E | 1.5 | 1.2 | 2.0 | <1.0 | 0.4 | 2.0 |
| RPC040 I-10 | 3-pyridyl | H | E | 22.0 | 18.0 | 18.0 | 22.0 | 0.9 | 14.0 |
| RPC041 I-11 | 4-pyridyl | H | E | 58.0 | 56.0 | 79.0 | 71.0 | 11.0 | 70.0 |
| RPC046 I-12 | CH$_3$ | CH$_3$ | — | 0.3 | 0.6 | 1.6 | 2.8 | 0.2 | 0.2 |
| RPC052 I-13 | 2-pyridyl | 2-pyridyl | — | 0.3 | 0.3 | 0.8 | <1.0 | 0.2 | 0.9 |

TABLE II-continued

In vitro activity of compounds Ia against human tumor cell lines.
Cytotoxicity $GI_{50}$ (μM)

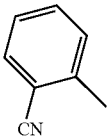

| Compd | R1 | R2 | Config | K562 | HeLa | HT-29 | HCT-15 | Caco-2 | MCF-7 |
|---|---|---|---|---|---|---|---|---|---|
| RPC056 I-14 | 2-cyanophenyl | H | E | 0.7 | 0.8 | 1.2 | <1.0 | 0.8 | 1.9 |
| RPC057 I-15 | 5-methylthiophene | H | E | 19.0 | 4.3 | 16.0 | 5.0 | 1.8 | 16.0 |
| RPC058 I-16 | phenyl | H | E | 15.0 | 3.0 | 13.0 | 5.5 | 7.6 | 10.0 |
| RPC059 I-17 | phenyl | $CH_3$ | E | 5.0 | 1.6 | 2.6 | 4.6 | 3.1 | 3.1 |

TABLE III

In vitro activity of compounds Ib against human tumor cell lines
Cytotoxicity $GI_{50}$ (μM)

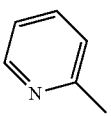

| Compd | $R_1$ | $R_2$ | $R_3$ | Config | K562 | HeLa | HT-29 | HCT-15 | Caco-2 | MCF-7 |
|---|---|---|---|---|---|---|---|---|---|---|
| RPC042 I-18 | 2-methylpyridine | H | H | E | 2.3 | 1.9 | 3.5 | 2.0 | 2.2 | 3.2 |

TABLE III-continued

In vitro activity of compounds Ib against human tumor cell lines
Cytotoxicity $GI_{50}$ (μM)

| Compd | $R_1$ | $R_2$ | $R_3$ | Config | K562 | HeLa | HT-29 | HCT-15 | Caco-2 | MCF-7 |
|---|---|---|---|---|---|---|---|---|---|---|
| RPC047 I-19 | 2-methylpyridine | phenyl | H | E | 0.9 | 1.4 | 0.9 | <1.0 | 0.9 | 0.9 |
| RP079 I-20 | 2-methylpyridine | 2-methylpyridine | H | — | 0.1 | ND | ND | ND | ND | ND |
| RPC060 I-21 | 5-methylthiophene | H | H | E | 11.0 | 38.0 | 35.0 | 40.0 | 39.0 | 11.0 |
| RPC061 I-22 | 1H-pyrrole | H | H | E | 7.1 | 12.0 | 6.9 | 5.6 | >100 | 9.2 |
| RPC081 I-23 | 2-methylpyridine | 2-methylpyridine | $CH_3$ | — | 0.9 | ND | ND | ND | ND | ND |

Selected compounds were submitted for testing in the organ-specific panel of human tumor cell lines at the National Cancer Institute, Bethesda, Md. This screen utilized 60 human tumor cell lines, representing leukemia, melanoma, and cancers of the lung, colon, brain, ovary, kidney, prostate, and breast (Boyd, M. R., "Status of the NCI preclinical antitumor drug discovery screen". In *Principles and practice of oncology updates*; De Vita, V. T., Jr. Hellman, S., Rosenberg, S. A., Eds.; Lippincott: Philadelphia, Pa., 1989; Vol. 3, pp 1-12).

The $GI_{50}$ values obtained along with the mean graph midpoint (MG MID) values are summarized in Table IV. The MG MID value is the average of the $GI_{50}$ values for all the cell lines tested for drug concentrations in the range of $10^{-4}$-$10^{-8}$ M (See website domain: dtp.nci.nih.gov/dtp). As can be seen from the results in Table IV, all the compounds tested exhibited high growth inhibitory activity across all tested cell lines, with an MG MID of 0.228-0.977 μM. Cells found to be the most sensitive to compound I-9 (RPC038) were leukemia, prostate, ovarian, and renal cancer cell lines; the most sensitive to compound I-12 (RPC046) were prostate, ovarian, colon, and renal cancer cell lines; and to compound I-18 (RPC042), prostate, ovarian, CNS, and melanoma cancer cell lines.

TABLE IV

Inhibitory concentration ($GI_{50}$ values in μM) values and histological cancer types for compounds I-9, I-12 and I-18.

| Cancer type[a] | RPC038 I-9 | RPC046 I-12 | RPC042 I-18 |
|---|---|---|---|
| leukemia | 0.116 | 1.27 | 0.966 |
| NSCL | 0.269 | 0.786 | 1.23 |
| colon | 0.251 | 0.497 | 1.37 |
| CNS | 0.271 | 1.20 | 0.633 |
| melanoma | 0.347 | 1.90 | 0.753 |
| ovarian | 0.196 | 0.447 | 0.629 |
| renal | 0.219 | 0.516 | 1.48 |
| prostate | 0.137 | 0.363 | 0.598 |
| breast | 0.250 | 0.751 | 1.15 |
| MG-MID | 0.228 | 0.847 | 0.977 |

[a]Each cancer type represents the arithmetic mean of two to nine cancer cell lines (NSLC = nonsmall cell lung; CNS = central nervous system)

Compounds I-9, I-12, and I-18 were also tested against multidrug-resistant tumor cell lines such as KB-A1000, which expresses 43- and 97-fold resistance to vinblastine and doxorubicine, and HL60-VCR, which expresses 1300-, 620-, and 8-fold resistance to vincristine, vinblastine and doxorubicine. These compounds showed high activity against both MDR tumor cell lines, as reported in Table V, below.

TABLE V

Cytotoxicity ($GI_{50}$ values in µM) of compounds I-9, I-12 and I-18 on MDR tumor cells.

| | Doxorubicine | | Vincristine (VCR) | |
|---|---|---|---|---|
| Compound | Sensitive KB-3-1 | Resistant KB-A1000 | Sensitive HL60 | Resistant HL60-VCR |
| (RPC038) I-9 | 2.2 | 6.0 | 1.0 | 1.5 |
| (RPC046) I-12 | 0.8 | 4.0 | 1.8 | 2.2 |
| (RPC042) I-18 | 2.1 | 0.4 | 1.2 | 0.7 |

HL60/VCR-expressing 1300-, 620-, and 8-fold resistance to vincristine, vinblastine and doxorubicin and KB-A1000 expressing 43- and 97-fold resistance to vinblastine and doxorubicin, respectively were obtained from Prof. Ahmad R. Safa, Simon Cancer Center, Indiana University School of Medicine, Indianapolis, IN. Logarithmically growing cells (2 × $10^3$ cells/0.1 ml) were incubated in 96-well plates at 37° C. in an atmosphere of air and 5% $CO_2$. Compounds dissolved insaline were added 24 hr later and further incubated for 72 hr and treated with MTS reagent, 2 hr later read at 490 nm. (Ogretmen B. and Safa A. R., *Biochemistry*, vol. 39, 194-204 (2000); Shen, et al., *Mol Cell Biol*, vol. 6, 4039-4044 (1986)).

The results demonstrate that these compounds are potent antitumor agents against cell lines derived from cancers that are among leading causes of cancer mortality, including cancers such as colorectal, ovarian, renal, non-small cell lung, and CNS cancers.

To date, the putative mechanism(s) by which the novel hydrazone derivatives of the invention induce cell death is currently the subject of ongoing research (see, e.g., Example 25, below). Patterns of drug activity across the NCI-60 human cancer cell lines have been shown to contain detailed information that can be used to delineate the mechanism of action of new antitumor agents (Paull, et al., Display and analysis of patterns of differential activity of drugs against human tumor cell lines: development of mean graph and COMPARE algorithm. *J. Natl. Cancer Inst.* 81, 1088-1092 (1989); Weinstein, et al., *Science*, vol. 275, 343-349 (1997)). Antitumor agents with identical mechanisms of action are believed to possess identical or nearly identical cytotoxicity patterns. A Pearson correlation coefficient (PCC) with the COMPARE algorithm of >0.5 between an unknown and a known compound shows a similar mechanism of action. Using compound I-9 (NSC 752331) as a seed, a COMPARE analysis showed a negative correlation with antitumor agents of known mechanism of action, indicating that that the compounds of the invention represent a novel class of antitumor agents with a novel mechanism(s) of action.

Example 25

The example describes research elucidating a mechanism of action for certain of the novel hydrazones described herein.
Introduction
The newly synthesized hydrazones RPC038, RPC042, and RPC046 had shown anti-tumor activity against 60 human cancer cell lines panel of the National Cancer Institute and on multi-drug resistant cell lines. The present studies were conducted to evaluate their action on signal transduction pathways in human colorectal carcinoma HT29. All the three compounds were examined at their $IC_{50}$ doses.

Figure 2:
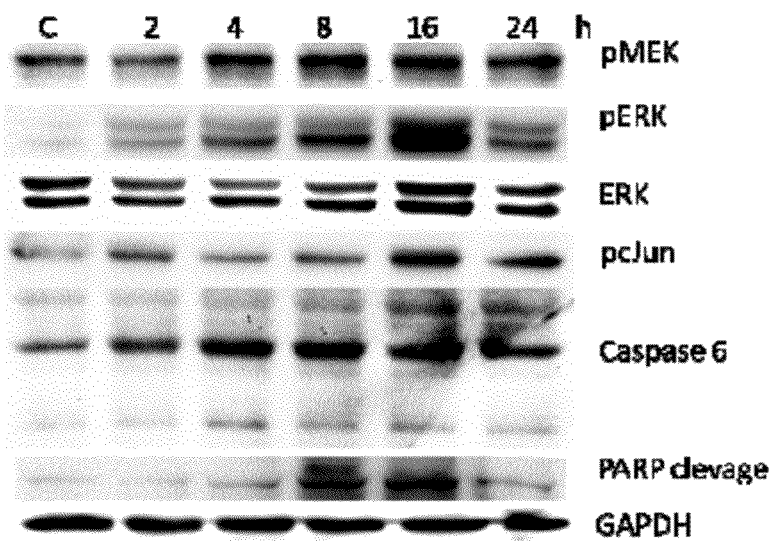
FIG. 2 is a gel showing the effects of compound RPC038 on HT29 cells.
Figure 3:
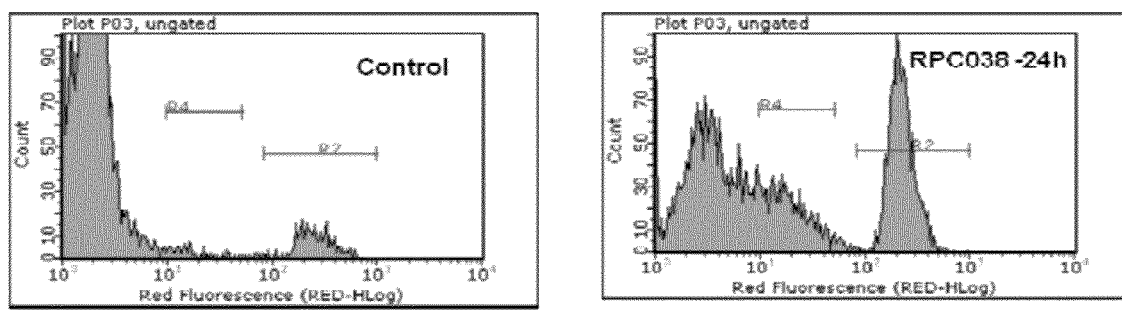
FIG. 3 shows two plots of a FACS analysis of control cells and cells treated with RPC038.
Figure 4:
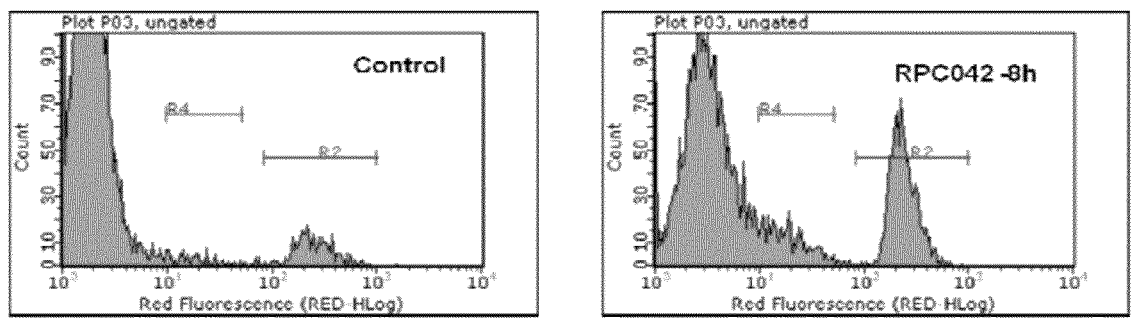
FIG. 4 shows two plots of a FACS analysis of control cells and cells treated with RPC042.

Methods
Human colorectal carcinoma HT29 cells were obtained from the National Cancer Institute, Bethesda, Md., USA, and maintained in 5% $CO_2$ at 37° C. in minimum essential media (Life Technologies, Inc., Grand Island, N.Y., USA) supplemented with 1% penicillin, streptomycin (Invitrogen, Carlsbad, Calif., USA), and 10% fetal bovine serum for optimal growth. HT29 cells ($1 \times 10^6$) were plated in 10 mm plates, and 24 h later, fresh media was added and treated with the RPC038, RPC042 and RPC046 for indicated time points (2, 4, 8, 16 and 24 h). The cells were then washed with cold phosphate buffered saline (PBS) and taken in 1 ml PBS on ice and centrifuged at 4° C. The pellet was resuspended in appropriate volumes of radio immunoprecipitation assay buffer with protease inhibitor, kept on ice for 45 min and subsequently centrifuged at 4° C. An aliquot of supernatant (protein extract) was used to estimate the protein concentration. An aliquot of protein extract (40 µg) was subjected to Western blot analysis on a 12% polyacrylamide gel and transferred to nitrocellulose membrane. Blots were blocked, incubated with primary anti-pMEK, pERK, pJNK, pcjun, ERK, JNK, Cjun, Caspase-8, Caspase-6, PARP cleavage, or GAPDH antibodies (Cell Signaling Technology, Danvers, Mass.) and then conjugated with a secondary anti-mouse or an anti-rabbit horseradish peroxide antibody, and detected by ChemiDoc™ XRS+ System with Image Lab™ Software.
Results
The results (FIGS. 1 and 2) with RPC038 and RPC042 showed a time dependent MEK activation at 2 h, followed by phosphorylation of ERK at 4 h without phosphorylation of JNK (results not shown), and activation of cjun was observed at 6 h. This activation was through ERK signaling and not through JNK signaling, resulting in PARP cleavage after 16 h. The initial studies also showed Caspase-3 activation through Caspase-6 and not through Caspase-8, indicating that the observed apoptosis is mediated by a mitochondrial pathway. Activation of NFkB (p50) was also observed following treatment with these compounds. Apoptosis was also established using Annexin-V, FACS analysis (FIGS. 3 and 4).
Conclusion
ERK activation controls various cell responses, such as proliferation, differentiation, and cell death. Depending on the cell type, ERK activation is associated either with intrinsic apoptotic pathway or extrinsic apoptotic pathway. These new hydrazone compounds can be used in combination with Doxorubicin in treating human hepatocellular carcinoma and human cervical adenocarcinoma. Further, these compounds can be combined with agents such as Shikonin and Taxol for treating human breast adenocarcinoma, as they activate both mitochondrial and extrinsic pathways for cancer cell death. These new compounds can also be used in combination with Sorafenib to treat colorectal cancer since these compounds can synergistically induce cancer cell death.

All patents, patent applications, and publications mentioned in the specification are indicative of the levels of those of ordinary skill in the art to which the invention pertains. Each patent, patent application, and publication cited herein is hereby incorporated by reference in its entirety for all purposes regardless of whether it is specifically indicated to be incorporated by reference in the particular citation.

All of the compounds, compositions, and methods disclosed and claimed herein can be made and executed without undue experimentation in light of the present disclosure. Moreover, it is intended to obtain rights which include alternative and/or equivalent embodiments to the extent permitted, including alternate, interchangeable, and/or equivalent structures, functions, ranges, or steps to those claimed, whether or not such alternate, interchangeable and/or equivalent structures, functions, ranges, or steps are disclosed herein, and without intending to publicly dedicate any patentable subject matter, as it is intended that all patentable subject matter disclosed herein eventually be the subject of patent claims.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Also, the invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Furthermore, while the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of treatment for cancer, comprising administering a composition comprising a carrier, optionally a pharmaceutically acceptable carrier, and a compound of formula (I) to a subject in need of treatment therewith, wherein the compound of formula (I) has a structure:

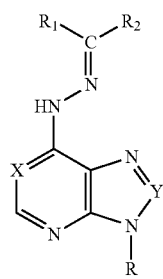

I wherein X is N or CH;
wherein Y is N or C—$R_3$, where $R_3$ is H, alkyl, cycloalkyl, phenyl, or substituted phenyl, benzyl, or substituted benzyl, F, Cl, Br, I;
wherein R is (i) H, alkyl, cycloalkyl, phenyl, or substituted phenyl, benzyl, 2-hydroxyethyl, 3-hydroxypropyl, 2,3-dihydroxypropyl, alkoxyalkyl, carboxyalkyl or (ii)

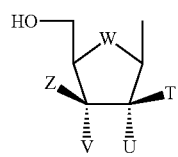

wherein W is O, S, or $CH_2$; U is H, OH, F, or Cl; V is H, OH, F, or Cl; T is H, $CH_3$, F, Cl, or OH; and
Z is H, $CH_3$, OH, F, Cl;
wherein $R_1$ in compound of formula I is (i):
H, alkyl, cycloalkyl, phenyl, benzyl, dihydroxyethyl, dihydroxypropyl, carboxy, carboxyalkyl, $COOR_3$, $(CH_2)_n COOR_3$, where $R_3$ is an aliphatic residue or a phenyl group; or
$R_1$ is a heterocycle selected from the group consisting of:

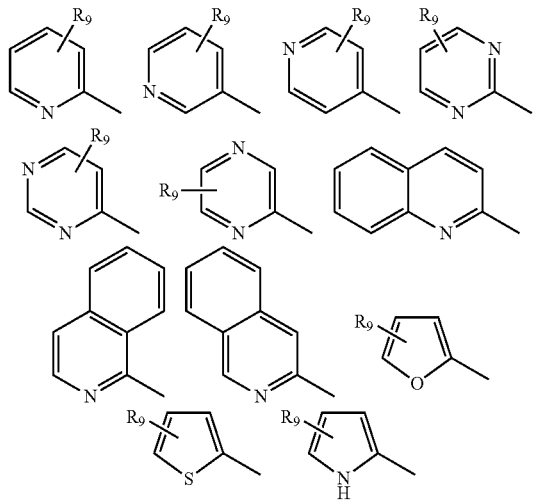

wherein $R_9$ is H, $CH_3$, $OCH_3$, OH, Cl, Br, F, $CF_3$, $NO_2$, $NH_2$, $NHCOCH_3$, $N(CH_3)_2$, CN, C=NH($NH_2$), C=S ($NH_2$), C=NH(NHOH), COOH, or $COOR_6$, wherein $R_6$ is an aliphatic residue or a phenyl group, or $CONR_7R_8$, wherein $R_7$, $R_8$ represent H, an aliphatic substituent, or a phenyl group;
wherein $R_2$ in the compound of formula I is (i) H, alkyl, cycloalkyl, phenyl, benzyl, dihydroxyethyl, dihydroxypropyl, carboxy, carboxyalkyl, $COOR_3$, $(CH_2)_n COOR_3$ where $R_3$ an aliphatic residue or a phenyl group; or (ii) a heterocycle selected from the group consisting of:

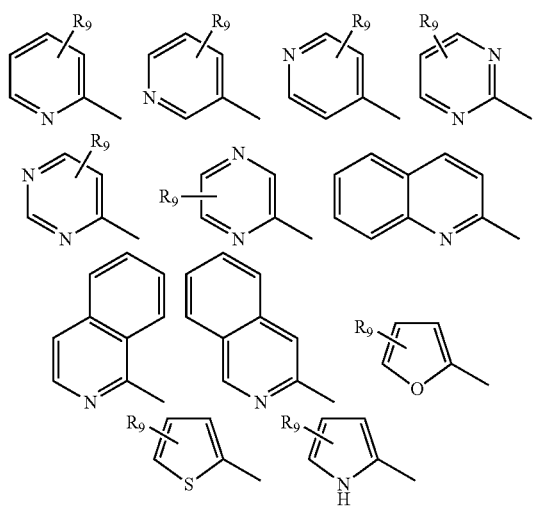

wherein $R_9$ is H, $CH_3$, $OCH_3$, OH, Cl, Br, F, $CF_3$, $NO_2$, $NH_2$, $NHCOCH_3$, $N(CH_3)_2$, CN, C=NH($NH_2$), C=S ($NH_2$), C=NH(NHOH), COOH, or $COOR_6$, wherein $R_6$ is an aliphatic residue or a phenyl group, or $CONR_7R_8$, wherein $R_7$, $R_8$ represent H, an aliphatic substituent or a phenyl group;

wherein in the compound of formula I:

"alkyl" is a branched or unbranched, saturated, or unsaturated, monovalent or multivalent hydrocarbon group, optionally selected from the group consisting of a methyl, ethyl, propyl, isopropyl, butyl, isobutyl, t-butyl, pentyl, hexyl, heptyl, decyl, ethenyl, propenyl, butenyl, isobutenyl, pentenyl, hexenyl, heptenyl, octenyl, nonenyl, decenyl, ethynyl, propynyl, butynyl, isobutynyl, pentynyl, hexynyl, heptynyl, octynyl, nonynyl, and decynyl group;

"cycloalkyl" is a non-aromatic, monocyclic, or polycyclic ring comprising carbon and hydrogen atoms comprising one or more carbon-carbon double bonds, optionally selected from the group consisting of a cyclopropyl, cyclobutyl, cyclopentyl, cyclohexyl, and cycloheptyl, and saturated cyclic and bicyclic terpenes and cycloalkenyl groups such as cyclopropenyl, cyclobutenyl, cyclopentenyl, cyclohexenyl, cycloheptenyl, and unsaturated cyclic and bicyclic terpenes, wherein the cycloalkyl group is unsubstituted or substituted by one or two suitable substituents; and "phenyl" is a substituted or disubstituted phenyl group selected from the group consisting of:

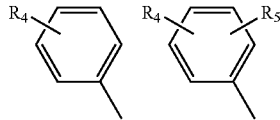

wherein each of $R_4$ and $R_5$ independently is H, $CH_3$, $OCH_3$, OH, Cl, Br, F, $CF_3$, $NO_2$, $NH_2$, $NHCOCH_3$, $N(CH_3)_2$, CN, C=NH($NH_2$), C=S(NH), C=NH(NHOH), COOH, or $COOR_6$, wherein $R_6$ is an aliphatic residue or a phenyl group, or $CONR_7R_8$, wherein $R_7$, $R_8$ represent H, an aliphatic substituent or a phenyl group;

or salt thereof.

2. A method according to claim 1, wherein the cancer is selected from the group consisting of hepatocellular carcinoma, cervical adenocarcinoma, breast adenocarcinoma, and colorectal cancer.

3. A method according to claim 1, wherein the treatment is a combination therapy that comprises administering a second chemotherapeutic agent, optionally selected from the group consisting of Shikonin, Paclitaxel, and Sorafenib.

* * * * *